US005859226A

United States Patent [19]
Hunt et al.

[11] Patent Number: 5,859,226
[45] Date of Patent: Jan. 12, 1999

[54] POLYNUCLEOTIDE DECOYS THAT INHIBIT MHC-II EXPRESSION AND USES THEREOF

[75] Inventors: C. Anthony Hunt; Carol Lim, both of San Francisco; Marvin R. Garovoy, San Anselmo, all of Calif.

[73] Assignee: Regents of the University of California, The, Oakland, Calif.

[21] Appl. No.: 281,423

[22] Filed: Jul. 27, 1994

Related U.S. Application Data

[63] Continuation-in-part of Ser. No. 100,088, Jul. 29, 1993, abandoned.

[51] Int. Cl.$^6$ .................................................. C07H 21/04
[52] U.S. Cl. .............................. 536/24.1; 514/44; 514/6; 514/172.3; 514/325; 514/91.1; 514/1.2
[58] Field of Search ................................... 514/44; 435/6, 435/91.1, 91.2, 172.3, 325; 536/23.1, 24.1; 935/33, 34

[56] References Cited

FOREIGN PATENT DOCUMENTS

| | | |
|---|---|---|
| 0601585 | 6/1994 | European Pat. Off. . |
| WO 90/12812 | 11/1990 | WIPO . |
| WO 92/18522 | 10/1992 | WIPO . |
| WO 92/19732 | 11/1992 | WIPO . |
| WO 93/02188 | 2/1993 | WIPO . |
| WO 93/14768 | 8/1993 | WIPO . |

OTHER PUBLICATIONS

Ono, S.J. et al., "Transcription of a subset of human class II major histocompatibility complex genes is regulated by a nucleoprotein complex that contains c–fos or an antigenically related protein" *Proc. Natl. Acad. Sci.* (*USA*) (1991) 88:4304–4308.
Reith, W. et al., "MHC class II regulatory factor RFX has a novel DNA–binding domain and a functionally independent dimerization domain" *Genes Dev.* (1990) 4(9):1528–1540.
Hasegawa, S.L. et al., "Regulatory factor–X binding to mutant HLA–DRA promoter sequences" *Nucleic Acid Res.* (1991) 19(6):1243–1249.
Faustman, D. et al., "Prevention of xenograft rejection by masking donor HLA Class I antigens" *Science* (1991) 252:1700–1702.
Cook, P.D., "Medicinal chemistry of antisense oligonucleotides—future opportunities" *Anti–Cancer Drug Des.* (1991) 6(6):585–607.
Crooke, R.M., "In vitro toxicology and pharmacokinetics of antisense oligonucleotides" *Anti–Cancer Drug Des.* (1991) 6(6):609–646.
Holt, J.T., "Cutting the chain of command: Specific inhibitors of transcription" *Antisense Res. & Dev.* (1991) 1(4):365–369.
Chu, B.C.F. et al., "Binding of hairpin and dumbbell DNA to transcription factors" *Nucleic Acid Res.* (1991) 19(24):6958.
Chu, B.C.F. et al., "The stability of different forms of double–stranded decoy DNA in serum and nuclear extracts" *Nucl. Acids Res.* (1991) 20(21):5857–5858.

Wemmer, D.E. et al., "Preparation and melting of single strand circular loops" *Nucleic Acids Res.* (1985) 13(23):8611–8621.
Erie, D.A. et al., "Melting behavior of a covalently closed, single–stranded, circular DNA" *Biochem.* (1989) 28(1):268–273.
Snowden–lfft, E.A. et al., "Characterization of the structure and melting of DNAs containing backbone nicks and gaps" *Biochem.* (1990) 29(25):6017–6025.
Reith, W. et al., "RFX1, a transactivator of hepatitis B virus enhancer I, belongs to a novel family of homodimeric and heterodimeric DNA–binding proteins" *Mol. & Cell. Biol.* (1994) 14(2):1230–1244.
Siegrist, C.A. et al., "RFX1 is identical to enhancer factor C and functions as a transactivator of the hepatitis B virus enhancer" *Mol. & Cell. Biol.* (1993) 13(10):6375–6384.
Erie, D. et al., "A dumbbell–shaped, double–hairpin structure DNA: A thermodynamic investigation" *Biochem.* (1987) 26(22):7150–7159.
Gray, P.W. et al., "Structure of the human immune interferon gene" *Nature* (1982) 298:859–863.
Lotteau, V., "Modulation of HLA Class II antigen expression by transfection of sense and antisense DRα cDNA" *J. Exp. Med.* (1989) 169:351–356.
Izant, J.G. et al., "Constitutive and conditional suppression of exogenous and endogenous genes by anti–sense RNA" *Science* (1985) 229:345–352.
Uhlmann, E. et al., "Antisense oligonucleotides: A new therapeutic principle" *Chem. Rev.* (1990) 90(4):544–584.
RW Wagner (1994) Nature 372:333–335.
Stull et al. (1995) Pharmaceutical Res., vol. 12, No. 4:465–483.
Trisha Gura (1995) Science, vol. 270:575–577.
Steime et al. (1996) Advances in Imm., 61:327–334.
Siegrist et al. (1993) European J. Imm., 23, 11:2903.
Hasegawa et al. (1991) Nuc. Acid Res., 19, 22:6269.
Golub et al. (1991) Immunology A Synthesis, Sinauer Assoc. Inc., p. 663–667.

*Primary Examiner*—Christopher S.F. Low
*Assistant Examiner*—Dave Trong Nguyen
*Attorney, Agent, or Firm*—Morrison & Foerster LLP

[57] ABSTRACT

The invention is directed to a newly discovered class of polynucleotide decoys that is capable of competitively inhibiting the binding of transcription factors to the X-box sequence. This binding is necessary for the expression of MHC-II genes. The invention is also directed to methods of preparing these polynucleotide decoys, and methods of use thereof. In particular, we have identified a class of polynucleotide decoys that mimic the X-Box of MHC-II and competitively bind the MHC-II transcription factor RF-X, resulting in the modulation of MHC-II antigen expression. Thus, the invention can be used to inhibit the expression of HLA molecules on the surface of donor cells or organs, in order to render them invisible to the host's immune system, or in methods of treating an individual with an autoimmune disease characterized by dysfunctional expression of an MHC class II antigen. Further, because of the role of RF-X in the expression of several viral proteins, the polynucleotide decoys of the invention can be used in methods of treating an individual infected with hepatitis B virus, or cytomegalovirus.

2 Claims, 7 Drawing Sheets

POLYNUCLEOTIDE DECOYS THAT INHIBIT MHC-II EXPRESSION AND USES THEREOF

CROSS-REFERENCE TO A RELATED APPLICATION

This application is a continuation-in-part of U.S. patent application Ser. No. 08/100,088, filed Jul. 29, 1993, now abandoned the disclosure of which is incorporated herein by reference.

TECHNICAL FIELD

This invention relates to nucleotide therapeutics, transplantation and immunology. More specifically, it relates to a newly discovered class of polynucleotide decoy molecules and methods for making cells and organs that are less likely to be rejected when transplanted into a recipient host using these polynucleotide decoys, which are capable of binding to a specific gene regulatory factor and reducing the expression of MHC class II transplantation antigens.

BACKGROUND OF THE INVENTION

Among gene products that relate to transplantation antigens are the products of the Human Leukocyte Antigen (HLA) complex, also known as the major histocompatibility complex (MHC), located on the short arm of chromosome 6. The HLA antigens are divided into two classes depending on their structure. The genetic loci denoted HLA-A -B, and -C code for the HLA Class I antigens, and HLA-DP, -DQ and -DR code for the HLA Class II antigens.

HLA Class II molecules are composed of two non-covalently linked glycoproteins, the a chain and the highly polymorphic β chain. Each chain contains one extracellular domain, a transmembrane segment and a cytoplasmic tail. The structure of the α and β chains and their genes have been elucidated. All known Class II genes are similar in structure and encoded by exons 1–4, with exon 5 coding for an untranslated region. The DP, DQ and DR loci all consist of multiple genes. A total of twelve class II genes have been identified. In some haplotypes, some class II genes do not code for a functional peptide and are classified as pseudogenes.

Regulation of HLA class II antigen expression occurs in part through a series of promoter regions such as the J, W, X (including $X_1$ and $X_2$), and Y boxes, and the gamma interferon response element. The X (including $X_1$ and $X_2$) and Y boxes are known to be required in the transcriptional regulation of all class II promoters. Ono, S. J. et al., *Proc. Natl. Acad. Sci. (USA)* (1991) 88: 4304–4308.

Transcription of HLA-DRα Class II can be activated by RF-X (Regulatory Factors-X) which binds to the X-box region (−110 to −95) of the DRα promoter. RF-X and its binding site, the X-box are unique and have a high specificity for each other. The DNA binding domain of RF-X consists of 91 amino acids with a basic stretch and shares no notable homology with other known DNA binding motifs (Reith et al. (1990), *Genes Dev.*, Vol. 4(9), pp. 1528–40). RF-X binds only the X-box; substitutions in the X-box are generally not well tolerated by RF-X. (Hasegawa et al. (1991), *Nucleic Acids Res.*, Vol 19(6), pp. 1243–49). The X-box sequence is an atypical promoter site, being neither palindromic nor dyad symmetric. Additionally no other sequence (using the program Eugene) shows exact homology with the X-box. The X-box is conserved in humans. No other known cloned transcription factors bind to this entire region of the X-box in the same manner.

HLA antigens are implicated in the survival of cell grafts or transplants. Although there is acceptable graft survival in the first year for nearly all types of transplants, by five and ten years after transplantation only 40–50% of all grafts are still functioning. This low rate is due to the relentless attack of the immune system on the graft. In addition, death rates of 1–5% are recorded even at the best transplant centers. Drugs are commonly used to control immune responses and prevent graft rejection, and death is often an indirect result of this drug administration.

The drugs used to control immune responses usually cause a non-specific depression of the immune system. A patient with a depressed immune system is far more susceptible to develop life-threatening infections and a variety of neoplasia. The low rate of long term success, and serious risks of infection and cancer are the two main challenges now facing the entire field of tissue and organ transplantation.

It has been suggested that graft rejection can be prevented or reduced by reducing the levels of exposed HLA antigens on the surface of transplant cells. Faustman, D. et al., *Science* (1991) 252:1700–1702, observed that xenograft survival was increased by masking HLA class I surface antigens with $F(ab')_2$ antibody fragments to HLA class I or tissue specific epitopes.

One way to reduce the level of cell surface transplantation antigens is to retard (downregulate) the expression of the transplantation antigen genes.

Generally, eucaryotic gene expression may be regulated at any of the steps from DNA transcription to RNA translation to protein; and it is generally agreed that gene expression is at the level of transcription. In order for transcription to occur, transcription factors must bind distinct regulatory sites or promoters on the gene. Once bound, transcription factors may interact with RNA polymerase or other factors to activate or repress transcription. Some transcription factors are constitutively expressed in specific cells while others may be transiently activated in response to various physiological signals (such as cAMP, IFN-γ, etc.). Thus in a given cell transcription of particular genes depends on which transcription factors are present in that cell type and/or whether the signals to activate the transcription factors are present.

Agents such as actinomycin (an intercalator) have been used to block transcription in a nonspecific manner. A variety of approaches to sequence-specific gene modulation include use of antisense oligonucleotides and antigene oligonucleotides (triple helix formers). These are limited in general or in particular instances. Antisense oligonucleotides block gene expression by targeting mRNA while triple helix forming oligos target double-stranded DNA. Inaccessibility of the target mRNA due to RNA secondary structure can limit the usefulness of antisense methods; triple helix approaches are limited by poor nuclear access, chromatin structure (bypassing histones), and the need for targeting a homopurine-homopyrimidine stretch. Degradation of oligonucleotides by exonucleases an excessive binding to untargeted cellular factors can limit the effectiveness of both antisense and triple helix methods. Chemical modification of oligos can improve nuclease resistance but can also result in increased toxicity, reduced binding affinity, and lower activity (Cook 1991, Crooke 1991).

J. T. Holt (1991),*Antisense Res. Dev.*, Vol. 1(4), pp. 65–9, has shown that by providing excess DNA binding sites, specific transcription factors can be quenched and are thereby prevented from binding to endogenous DNA.

Chu et al. (1991) *Nucl. Acids Res.* 19: 6958, describe DNA structures in "hairpin" and "dumbbell" configurations containing CRE and TRE sequences, and reported using them in vitro as substitutes for regular double-stranded DNA to bind CREB and JUN, respectively, in gel shift assays.

Chu et al. (1992) *Nucl. Acids Res.* 21: 5857–5858, demonstrate that in nuclear extracts, dumbbell DNA is much more stable than double-stranded or hairpin DNA. However, the nicking of dumbbell DNA in human serum, caused by endonuclease degradation of the single-stranded loops, is a potential problem, since it converts dumbbell DNA to a double-stranded form that is no more stable in the nucleus than standard double-stranded DNA molecules.

International patent publication WO92/19732 describes "closed" oligonucleotides that can be used as "sense" or "antisense" molecules, with the advantage of being resistant to exonucleases. Among the variety of "closed" structures are "dumbbell" configurations in which the ends are closed by virtue of addition links of thymidine nucleotides. Use of the closed "sense" oligonucleotides to bind protein factors having as affinity for RNA or DNA sequences or structures is suggested.

Single-strand circular DNA where a portion becomes double-stranded have been used as an experimental system for studying local thermal stability in DNA (Wemmer et al. (1985), *Nucl. Acid. Res.*, Vol. 13(23), pp. 8611–21); as models for hairpins and cruciforms (Erie et al. (1989), *Biochemistry*, Vol. 28(1), pp. 268–73; and as models for comparison to nicked or gapped DNA (Snowden-Ifft et al. (1990), *Biochemistry*, Vol. 29(25), pp. 6017–25).

SUMMARY OF THE INVENTION

We have discovered a class of polynucleotide decoys that competitively bind transcription factors necessary for transcription of MHC-II genes. Particularly, for example, we have identified oligonucleotides that mimic the X-Box of MHC-II and that competitively bind the MHC-II transcription factor RF-X. Exposing the cell to such an oligonucleotide can result in production of a MHC-II-depleted cell. That is, the polynucleotide decoys of the invention act as modulators of MHC-II expression. The invention can be used, therefore, to inhibit the expression of HLA molecules on the surface of donor organ/cell, in order to reduce its visibility to the host's immune system.

The polynucleotide decoy of the invention is a centrally double-stranded (but potentially lacking as many as two base pairings), "dumbbell" shaped structure, with linking cap oligonucleotides that is covalently closed in some embodiments and in other embodiments is linear. The single-stranded caps linking each of the two ends of the polynucleotide decoy are present to stabilize the structure, prevent degradation by exonucleases, and are not intended to be involved in recognition of the protein of interest. Compared to antisense and antigene approaches, target inaccessibility may be of less concern for the polynucleotide decoy, because its target is a protein which may be found in the cytoplasm as well as the nucleus. Lower doses of the polynucleotide decoy may suffice to effectively block transcription of the gene of interest, as compared for example to dosages of nucleotides required for an antisense approach, because transcription factors are ordinarily present in low copy number.

Preferred polynucleotide decoys are short covalently closed nucleotides, with an entirely double-stranded internal segment, and wherein the polynucleotide decoys have a sequence that mimics the double-stranded sequence of the X-box, with polythymidine segments linking the ends together. Administration of a polynucleotide of the invention results in downregulation of HLA II DRα proteins or mRNA. The polynucleotide decoys of the invention can be useful in regulating gene expression in the HLA system and in other systems as well.

The invention contemplates the development of a "universal donor cell" reduced in one or more HLA antigens by treatment of the cell with a polynucleotide decoy of the invention. The absence of certain HLA antigens on the surface of donor cells, tissues or organs comprising these cells will cause them not to be recognized as foreign and not to elicit a rejection response. By the selective introduction of polynucleotide decoys into a cell it is possible to block the expression of MHC class II genes, particularly constitutive expression, thereby rendering a graft "invisible" to the immune system. Thus, the problem of rejection is eliminated without nonspecific suppression of the immune system, and the immune system remains active to defend against infection and neoplasia. By implementing the methods of the present invention, even xenogeneic donor cells, tissues and organs can be rendered "invisible" to the immune system. Thus, the target cells or organs of the present invention may be derived from non-human mammalian species, made into transplantation antigen-depleted cells or universal donor organs, respectively, by a method of the invention, and subsequently transplanted into a human individual.

In particular the present invention embodies a class of polynucleotide decoys which comprise: (a) an internal oligonucleotide (I) having a length of X bases, where X is a number from about 10 to about 40; (b) two cap oligonucleotides ($P_1$ and $P_2$), each having a length of from about 3 to about 8 bases, wherein each of said cap oligonucleotides is comprised of bases which are unable to bind to any other base within the same cap oligonucleotide; (c) a first complementary oligonucleotide ($C_1$) having a length of Q bases, where Q is a number from about 5 to (X–5), said $C_1$ having a 3' to 5' nucleic acid sequence capable of Watson-Crick-type binding to the first Q bases in the 5' to 3' nucleic acid sequence of said I; and (d) a second complementary oligonucleotide ($C_2$) having a length of Z bases, where Z is a number greater than equal to about 5 and from ((X–(Q+ about X/8)) to (X–Q), said $C_2$ having a 5' to 3' nucleic acid sequence capable of Watson-Crick-type binding to the first Z bases in the 3' to 5' nucleic acid sequence of said I; wherein the 3' end of said $C_1$ is covalently linked to the 5' end of said $P_1$, the 3' end of said $P_1$ is covalently linked to the 5' end of said I, the 3' end of said I is covalently linked to the 5' end of said $P_2$, and the 3' end of said $P_2$ is covalently linked to the 5' end of said $C_2$; wherein at least one of the oligonucleotides selected from the group consisting of said $C_1$, said $C_2$, and said I, comprises an RF-X recognition sequence of Type-1 or Type-2; and wherein said polynucleotide decoy is capable of binding to an RF-X transcription factor.

The present invention also embodies methods of making the polynucleotide decoys of the invention comprising covalently linking oligonucleotides such that the resulting product has the structure of a polynucleotide decoy of the invention.

The present invention embodies methods for making an MHC-II-depleted cell from a target cell, the method comprising: (a) obtaining the target cell; and (b) exposing the target cell to a polynucleotide decoy of the invention, said polynucleotide decoy being preset in an amount sufficient to make the target cell a MHC-II-depleted cell. The present invention additionally embodies the MHC-II-depleted cells prepared by the fore-mentioned method.

The present invention further embodies polynucleotide decoys of the invention for use in the preparation of a composition for treating target cells to make them MHC-II-depleted cells.

The present invention further embodies MHC-II-depleted donor organs prepared by the method comprising: (a) obtaining a target organ from an individual; and (b) exposing the target organ to a polynucleotide decoy of the invention, said polynucleotide decoy being present in an amount sufficient to make the target organ a MHC-II-depleted donor organ.

The present invention further embodies methods of treating an individual with an autoimmune disease characterized by dysfunctional expression of an MHC class II antigen, the method comprising administering to that individual a polynucleotide decoy of the invention in an amount sufficient to inhibit expression of the MHC class II antigen.

The present invention also embodies methods of treating an individual infected with hepatitis B virus, the method comprising administering to that individual a polynucleotide decoy of the invention, in an amount sufficient to inhibit expression of hepatitis B surface antigen.

The present invention further embodies methods of treating an individual infected with cytomegalovirus, the method comprising administering to that individual a polynucleotide decoy of the invention in an amount sufficient to inhibit RF-X binding to the enhanced factor C sites of the cytomegalovirus genome.

The present invention further embodies methods of using a polynucleotide decoy to obtain a substantially purified, covalently closed polynucleotide decoy, comprising the steps of: (a) providing a linear polynucleotide decoy of the invention; (b) treating said linear polynucleotide decoy with a kinase enzyme, thereby obtaining 5' phosphorylated polynucleotide decoy; (c) heating said 5' phosphorylated polynucleotide decoy to inactivate said kinase enzyme, thereby obtaining heated, 5' phosphorylated polynucleotide decoy; (d) cooling said heated, 5' phosphorylated polynucleotide decoy mixture slowly to facilitate intramolecular annealing, thereby obtaining cooled, 5' phosphorylated polynucleotide decoy; (e) treating said cooled, 5' phosphorylated polynucleotide decoy with a ligating enzyme, thereby obtaining a covalently closed polynucleotide decoy; and (f) purifying said covalently closed polynucleotide decoy, thereby obtaining a substantially purified, covalently closed polynucleotide decoy.

The present invention also embodies nucleic acids comprising a linear polynucleotide decoy of the invention.

The present invention further embodies host cells comprising a nucleic acid comprising a linear polynucleotide decoy of the invention.

DETAILED DESCRIPTION OF THE INVENTION

Figure 1:
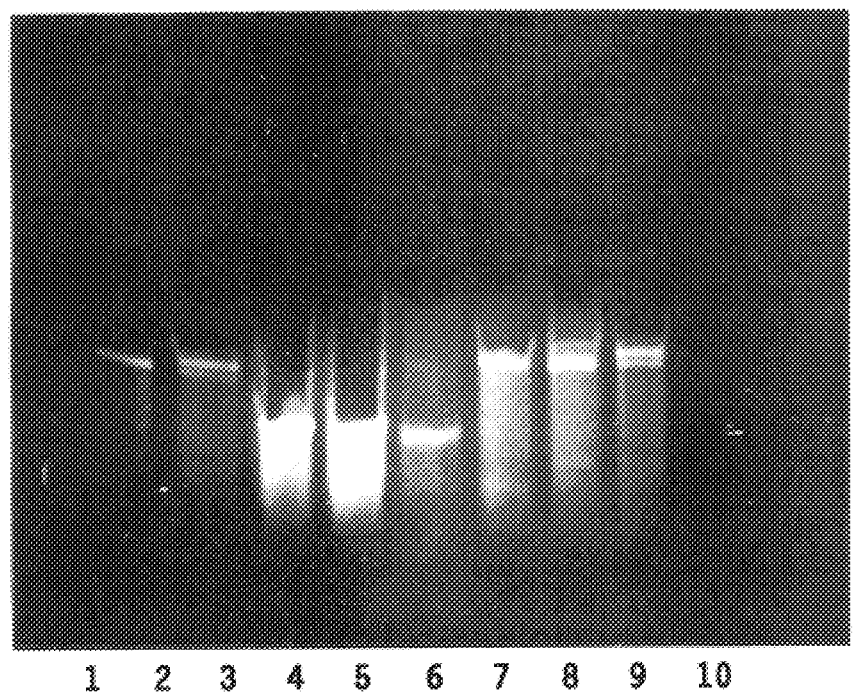
FIGS. 1–4 are half-tone reproductions from minigels, visualized with ethidium bromide on an ultraviolet illuminator, showing migration of, and degradation of, the 42-mer oligonucleotide and the polynucleotide decoy, both untreated (FIG. 1) and following various enzymatic treatments, namely (FIG. 2) klenow fragment, (FIG. 3) shrimp alkaline phosphatase, and (FIG. 4) S1 nuclease.

The present invention provides an improved source of transplantable cells for medical treatment. These transplantation antigen-depleted cells give rise to improved graft survival rates in the recipient or require lower levels of immunosuppressant drug administration in the recipient. These cells may also be useful in treating patients with autoimmune diseases.

The practice of the present invention encompasses conventional techniques of chemistry, molecular biology, biochemistry, protein chemistry, and recombinant DNA technology, which are within the skill of the art. Such techniques are explained fully in the literature. See, e.g., *Oligonucleotide Synthesis* (M. J. Gait ed. 1984); *Nucleic Acid Hybridization* (B. D. Hames & S. J. Higgins, eds., 1984); Sambrook, Fritsch & Maniatis, *Molecular Cloning: A Laboratory Manual*, Second Edition (1989); *PCR Technology* (H. A. Erlich ed., Stockton Press); R. K. Scope, *Protein Purification Principles and Practice* (Springer-Verlag); and the series *Methods in Enzymology* (S. Colowick and N. Kaplan eds., Academic Press, Inc.).

All patents, patent applications and publications mentioned herein, whether supra or infra, are hereby incorporated by reference in their entirety.

DEFINITIONS

As used herein, the term "transplantation antigen" is used to refer to antigenic molecules that are expressed on the cell surface of transplanted cells, either at the time of transplantation, or at some point following transplantation. Generally these antigenic molecules are proteins and glycoproteins. The primary transplantation antigens are products of the major histocompatibility complex (MHC), located on chromosome 6 in humans. The human MHC complex is also called the human leukocyte antigen (HLA) complex. MHC antigens are divided into MHC class I antigens (in humans, this class includes HLA-A, -B, and -C antigens) and MHC class II antigens (in humans, this class includes HLA-DP, -DQ, and -DR antigens). Thus, the terms "MHC-II antigens", "MHC class II antigens", and "MHC class II transplantation antigens" are used interchangeably herein to refer to the class of proteins, which in humans, includes HLA-DP, -DQ and -DR antigens. While the terms "MHC class II genes" and "MHC-II genes" are used interchangeably herein to refer to the genes which encode the MHC class II transplantation antigens. The term "MHC-II" is used herein to refer to the gene locus which encodes the MHC class II transplantation antigens, as well as the group of proteins encoded by that locus. Transplantation antigens also include cell surface molecules other than MHC class I and II antigens. These antigens include the following: (1) the ABO antigens involved in blood cell recognition; (2) cell adhesion molecules such as ICAM, which is involved in leukocyte cell-cell recognition; and (3) $\beta_2$-microglobulin, a polypeptide associated with the 44 kd heavy chain polypeptide that comprises the HLA-I antigens but is not encoded by the MHC complex.

As used herein, the term "transplantation antigen nucleotide sequence" refers to nucleotide sequences associated with genes encoding transplantation antigens. Nucleotide sequences associated with genes include the region of the gene encoding the structural product, including intron and exon regions, and regions upstream of the structural gene associated with transcription, transcription initiation (including transcription factor binding sites), translation initiation, operator and promoter regions, ribosome binding regions, as well as regions downstream of the structural gene, including termination sites. Nucleotide sequences associated with genes also include sequences found on any form of messenger RNA (mRNA) derived from the gene, including the pre-mRNA, spliced mRNA, and polyadenylated mRNA.

As used herein, the term "MHC-II-depleted cell" refers to cells that are in some way depleted in the expression of at least one MHC class II transplantation antigen. This depletion may be manifested by a reduced amount of antigen present on the cell surface. Preferably, at least about 50%, more preferably about 80%, and even more preferably about 90% of the MHC-II antigen is eliminated at the cell surface. Most preferably, this depletion results in essentially total absence of the antigen at the cell surface. The amount of MHC-II antigens on the cell surface can be determined by a number of techniques known in the art. Usually such techniques make use of an antibody that specifically binds to the MHC-II antigen, wherein the antibody is linked to a compound that is easily quantified, such as a radionuclide, enzyme (e.g., horseradish peroxidase), or fluorescent dye. The techniques for measuring the amount of MHC-II antigens on the cell surface can be performed on living cells or on dead, fixed cell or tissue samples. Preferably the techniques are performed on living cells using a fluorescence-activated cell sorting analysis and fluorescently tagged antibodies that specifically bind to an MHC-II antigen.

The term "MHC-II-depleted donor organ", as used herein, refers to an organ comprising MHC-II-depleted cells. An MHC-II-depleted cell or an MHC-II-depleted donor organ will have at least one of two properties: (1) the cell or organ will survive in the transplant recipient for time periods significantly longer than normal cells; or (2) the cell or organ will survive in the transplant recipient for time periods commensurate to normal, or untreated, cells or organs, but will require lower doses of immunosuppressive agents to the transplant recipient.

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

Generally the terms "oligonucleotides", "polynucleotides", and "nucleic acids" are used herein to refer to "straight-chained" molecules, in which the individual nucleotides are joined by linking groups which bridge the 5' carbon of one nucleotide's sugar moiety to the 3' carbon of a second nucleotide's sugar moiety. Although "branch-chained" nucleic acids, including those with linking groups bridging carbons other than 3' and 5' of two nucleotide may be used in the invention, particularly in the attachment of targeting compounds to polynucleotide decoys. Thus, a single-stranded nucleic acid molecule can either be "linear" or "covalently closed". "Covalently closed" nucleic acids (or polynucleotide decoys) form a continuous circle of nucleotides without an end. In the case of "linear" nucleic acids or (polynucleotide decoys), there would be at least two ends, exactly two ends in a straight-chained molecule and more in a branch chained molecule. Therefore, a straight-chained "linear" nucleic acid or decoy would have both a "5' end", in which the 5' carbon of the terminal nucleotide is not joined to any other nucleotide, and a "3' end", in which the 3' carbon of the terminal nucleotide is not joined to any other nucleotide. The term "linear" is used herein to refer to any nucleic acid molecules regardless of the degree of folding or degree to which the bases of an individual molecule bind to one another.

The phrase "having a length of N bases" or "having a length of N nucleotides" is used herein to describe lengths along a single nucleotide strand, of a nucleic acid molecule, consisting of N individual nucleotides.

As used herein, the term "bind", in the phrase "bases which are unable to bind to any other base", refers to an interaction between the bases of an oligonucleotide which is mediated through base-base hydrogen bonding. One type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix.

The term "complementary" and "complementary oligonucleotide" are used herein to refer to oligonucleotides or portions of polynucleotides which are capable of forming Watson-Crick-type binding interactions with another particular oligonucleotide or particular region of a polynucleotide. Generally, unless otherwise noted, the use of the term "complementary" means that all of the bases of the shorter of the two nucleotides, or portions of the nucleotides being discussed, are capable of Watson-Crick-type binding to a particular region of the other longer, or equal sized, oligonucleotide.

The term "substantially purified" is used herein to describe a polynucleotide or polynucleotide decoy sample which has been separated from other compounds including, but not limited to other nucleic acids, and proteins (such as the enzymes used in the synthesis of the decoy), or the separation of covalently closed polynucleotide decoys from linear decoys. A polynucleotide decoy is substantially pure when at least about 60 to 75% of a sample exhibits a single polynucleotide sequence and conformation (linear versus covalently close). A substantially pure polynucleotide decoy typically comprises about 60 to 90% W/W of a nucleic acid sample, more usually about 95%, and preferably is over about 99% pure. Polynucleotide purity or homogeneity may be indicated by a number of means well known in the art, such as agarose or polyacrylamide gel electrophoresis of a sample, followed by visualizing a single polynucleotide band upon staining the gel, as exemplified in Example 7 below. For certain purposes higher resolution can be provided by using HPLC or other means well known in the art.

The "polynucleotide decoys" (also referred to herein as just "decoys") of the invention are derived from the DNA sequence of the X-box, the latter having a sequence as follows:

5'-CCCCTAGCAACAGATG-3' (SEQ ID NO:1)

3'-GGGGATCGTTGTCTAC-5' (SEQ ID NO:2)

The polynucleotide decoys of the invention comprise an internal oligonucleotide (I) having a length of X bases, where X is a number from about 10 to about 40, preferably 12 to 25, most preferably 14 to 20. The size of the I segments is bounded on the lower end by their ability to maintain the relative binding affinity of the larger segments to RF-X transcription factors. The size of the I segments is bounded on the upper end by their ability to remain relatively insensitive to endonucleases. Thus, the length limits of the I segment of a decoy can be determined empirically by one of skill in the art.

The polynucleotide decoys of the invention further comprise two cap oligonucleotides ($P_1$ and $P_2$), each having a length of from about 3 to about 8 bases, preferably 4 to 6 base most preferably 4 bases. Each of the cap oligonucleotides is comprised of bases which are unable to bind to any other base within the same cap oligonucleotide. Preferably each of the cap oligonucleotides consists of a single variety of nucleotide comprising a base selected from the group consisting of adenine, cytosine, thymidine, and modified nucleotides thereof. Most preferably both of the cap oligonucleotides consist of a single variety of nucleotide comprising a thymidine base.

The polynucleotide decoys of the invention further comprise a first complementary oligonucleotide ($C_1$) having a length of Q bases, where Q is a number from about 5 to (X–5), said $C_1$ having a 3' to 5' nucleic acid sequence capable of Watson-Crick-type binding to the first Q bases in the 5' to 3' nucleic acid sequence of said I. Thus, the entire $C_1$ segment beginning with its 3' end is able to bind to the first Q bases of the I segment beginning with its 5' end.

The polynucleotide decoys of the invention further comprise a second complementary oligonucleotide ($C_2$) having a length of Z bases, where Z is a number greater than equal to about 5 and from ((X–(Q+about X/8)) to (X–Q), said $C_2$ having a 5' to 3' nucleic acid sequence capable of Watson-Crick-type binding to the first Z bases in the 3' to 5' nucleic acid sequence of said I. Thus, the entire $C_2$ segment beginning with its 5' end is able to bind to the first Z bases of the I segment beginning with its 3' end, and the $C_1$ and $C_2$ segments are at least about five nucleotides in length. The minimal length of the complementary oligonucleotides is bounded on the lower end by their ability to effectively anneal to the I segment and maintain the polynucleotide decoy's relative insensitivity to exonucleases. Thus, a lower limit on the size of the $C_1$ and $C_2$ segments can be determined empirically by one of skill in the art. The upper limit on the size of each of the $C_1$ and $C_2$ segments is determined by the size of the I segment and the size of the other complementary oligonucleotide, such that the combined length of the $C_1$ and $C_2$ segments can not be longer than the I segment. However, there can be a gap between the $C_1$ and the $C_2$ segments, such that there are up to about one eighth the nucleotides of the I segment (X/8) which do not form Watson-Crick-type base pairing with any nucleotide of the $C_1$ and $C_2$ segments. Thus, a decoy of the invention comprising an I segment of 16 nucleotides in length could have a gap between its $C_1$ and $C_2$ segments of up to about 2 nucleotides. The maximal length of this gap is bounded by the decoy's relative insensitivity to exonucleases. Thus the maximal length of this gap between the $C_1$ and the $C_2$ segments can be determined empirically by one of skill in the art. Preferably the $C_1$ and $C_2$ segments are of roughly equal length, and the polynucleotide decoys of the invention contain no gap between the $C_1$ and the $C_2$ segments.

The oligonucleotides described above are covalently linked to form a polynucleotide decoy of the invention, wherein the 3' end of the $C_1$ segment is covalently linked to the 5' end of the $P_1$ segment, the 3' end of the $P_1$ segment is covalently linked to the 5' end of the I segment, the 3' end of the I segment is covalently linked to the 5' end of the $P_2$ segment, and the 3' end of the $P_2$ segment is covalently linked to the 5' end of said $C_2$.

Finally the polynucleotide decoys of the invention are comprised of an RF-X recognition sequence of Type-1 or Type-2, in at least one of the oligonucleotides selected from the group consisting of $C_1$, $C_2$, and I.

Reith et al. (1994) *Mol. and Cell. Biol.* 14: 1230–1244, demonstrated that the RF-X proteins comprise a family of DNA-binding proteins of which they have cloned three members, RF-X1, RF-X2, and RF-X3, from humans and mice. Members of the RFX family constitute the nuclear complexes that have been previously referred to as enhancer factor C, EP, methylation-dependent DNA-binding protein, and rpL30α. RF-X proteins share five strongly conserved regions which include the two domains required for DNA binding and dimerization, resulting in very similar DNA-binding specificities.

Reith et al. (1994) *Mol. and Cell. Biol.* 14: 1230–1244 have proposed a set of rules governing RF-X transcription factor binding to native double-stranded DNA sequences with the following consensus sequence: RTY*RYYAY*RGY*RAY(SEQ ID NO:3), where R is a purine, Y is a pyrimidine, and Y* is either a 5-methyl cytosine or a thymidine residue.

However, within a polynucleotide decoy of the present invention, an RF-X recognition sequence is derived from the following "decoy RF-X consensus sequence":

```
      1  2  3   4  5  6  7  8   9  10 11 12 13 14 15 16 17 18
5'-N  T  Y*  N  Y  N  R  Y*  N  N  N  N  A  Y  R  R  A  N-3' (SEQ ID NO:14)
``` where:
  N is any nucleotide;
  R is a nucleotide comprising a purine, preferably an adenine or guanine deoxyribonucleotide;
  Y is a nucleotide comprising a pyrimidine, preferably a cytosine or thymidine deoxyribonucleotide;
  Y* is a nucleotide comprising a 5-methylated pyrimidine, preferably a 5-methyl cytosine or a thymidine deoxyribonucleotide;
  A is a nucleotide comprising an adenine, preferably an adenine deoxyribonucleotide;
  the nucleotide at position 3 may also be any nucleotide comprising a pyrimidine, preferably a cytosine, a 5-methyl cytosine, or a thymidine deoxyribonucleotide; and the nucleotide at position 10 is preferably a nucleotide comprising guanine, more preferably a guanine deoxyribonucleotide.

The term "IRF-X recognition sequence" is used herein to refer to both "Type-1 RF-X recognition sequences" and "Type-2 RF-X recognition sequences", each defined hereafter.

As used herein, the term "Type-1 RF-X recognition sequence" refers to a nucleotide sequence, which: (1) has a span of the decoy RF-X consensus sequence of at least about 8 nucleotides in length; (2) comprises at least one of the spans selected from the following groups: (a) the nucleotides from positions 3 through 8 (5'-Y*-N-Y-N-R-Y*-31), and (b) the nucleotides from position 8 through 14 (5'-Y*-N-N-N-N-A-Y-3') of the decoy RF-X consensus sequence; and (3) may contain up to about 2 non-adjacent changes to the decoy RF-X consensus sequence, said changes being selected from the group consisting of (a) the insertion of a single nucleotide into a span of the decoy RF-X consensus sequence, (b) the deletion of a single nucleotide from the span of the decoy RF-X consensus sequence, and (c) the replacement of a single nucleotide of the span of the decoy RF-X consensus sequence for a spacer compound.

As used herein, the term "Type-2 RF-X recognition sequence" refers to a nucleotide sequence, which: (1) has a span of the decoy RF-X consensus sequence of at least 12 nucleotides in length; (2) comprises at least one of the spans selected from the following groups: (a) the nucleotides from positions 3 through 8 (5'-Y*-N-Y-N-R-Y*-3'), and (b) the nucleotides from position 5 through 14 (5'-Y-N-R-Y*-N-N-N-N-A-Y-3'(Residues 5 through 14 of SEQ ID NO:4) of the decoy RF-X consensus sequence; and (3) may contain up to 1 non-adjacent change to the decoy RF-X consensus sequence, said changes being selected from the group consisting of (a) the insertion of a single nucleotide into a span of the decoy RF-X consensus sequence, (b) the deletion of a single nucleotide from the span of the decoy RF-X consensus sequence, and (c) the replacement of a single nucleotide of the span of the decoy RF-X consensus sequence for a spacer compound.

Further, the polynucleotide decoys of the invention are capable of binding to an RF-X transcription factor. Such binding can be demonstrated by any method known in the art, including for example methods that directly measure binding like the Electrophoretic Mobility Shift Assay described below in Example 4, and the Gel Shift Assay described below in Example 8, as well as functional assays which indirectly demonstrate polynucleotide decoy/RF-X transcription factor binding like the CAT Assay described below in example 9.

Accordingly, a polynucleotide decoy of the invention mimics the X-box sequence, but is capped by short DNA oligonucleotides, preferably consisting of thymidine nucleotides, on the ends to improve resistance to exonucleases, for example:

(SEQ ID NO:5)

The polynucleotide decoys of the invention are linear in some embodiments and covalently closed in other embodiments. Initial experiments have indicated that the linear molecules have a marginally high affinity to RF-X transcription factors, while the covalently closed molecules have a marginally greater stability, being less sensitive to exonucleases. Thus, the choice of linear versus covalently closed decoys can be made on the basis of the requirements of a particular method or use of the invention for affinity and stability.

The invention is particularly drawn to the polynucleotide decoys consisting essentially of an oligonucleotide selected from the group consisting of:

| | | |
|---|---|---|
| RF-X: | 5'-CTAGGGGTTTTCCCCTAGCAACAGATGTTTTCATCTGTTG-3' | (SEQ ID NO:6) |
| RF-X-2: | 5'-GACTGGGTTTTCCCAGTCCATACGAAGTTTTCTTCGTATG-3' | (SEQ ID NO:7) |
| 42 mer: | 5'-GCTAGGGGTTTTTCCCCTAGCAACAGATGTTTTTCATCTGTT-3' | (SEQ ID NO:8) |
| 42* mer: | 5'-CTAGGGGTTTTTCCCCTAGCAACAGATGTTTTTCATCTGTTG-3' | (SEQ ID NO:9) |
| hlyn site: | 5'-TAACAACTTTTGTTGTTATAGTAACTTTTGTTACTA-3' | (SEQ ID NO:10) |
| kB: and | 5'-TCCCTTGGTTTTCCAAGGGACTTTCCGCTTTTGCGGAAAG-3' | (SEQ ID NO:11) |
| 38 mer: | 5'-TGCTAGGTTTTTCCTAGCAACAGATGTTTTTCATCTGT-3' | (SEQ ID NO:12) | as well as the polynucleotide decoys formed by covalently linking the 3' end and the 5' end of an individual decoy such that it is covalently closed.

The polynucleotide decoys and other nucleic acids of the invention usually comprise the naturally-occurring bases, sugars and phosphodiester linkages. However, any of the hydroxyl groups ordinarily present in the sugars may be replaced by phosphonate groups, phosphate groups, protected by a standard protecting group, or activated to prepare additional linkages to additional nucleotides, or may be conjugated to solid supports. If the 5' and 3' terminal OH groups are free they may be phosphorylated or substituted with amines or organic capping group moieties of from 1 to 20 carbon atoms. Other hydroxyl groups may also be derivatized to standard protecting groups.

The individual nucleotides or oligonucleotides which comprise the polynucleotide decoys or other nucleic acids of the invention are usually covalently bonded by phosphodiester linkages, one or more of which may be replaced by alternative linking groups. Thus, the term "covalently linked" is used herein to refer to the joining of two or more nucleotides by phosphodiester linkages or alternative linking groups. These alternative linking groups include, but are not limited to embodiments wherein phosphate is replaced by P(O)S ("thioate"), P(S)S ("dithioate"), P(O)NR$_2$ ("amidate"), P(O)R, P(O)OR', CO or CH$_2$ ("formacetal"), wherein each R or R' is independently H or substituted or unsubstituted alkyl (1–20C) optionally containing an ether (—O—) linkage, aryl, alkenyl, cycloalkyl, cycloalkenyl or aralkyl. Not all linkages in an oligomer need to be identical.

Also included within this invention are synthetic procedures in which the resultant oligonucleotides or polynucleotide decoys of the invention include incorporation of analogous forms of purines and pyrimidines. "Analogous" forms of purines and pyrimidines are those generally known in the art, many of which are used as chemotherapeutic agents. An exemplary but not exhaustive list includes aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyl-uracil, 5-methoxyaminomethyl-2-thiouracil, beta-D-mannosylqueosine, 5-methoxyuracil, 2-methyl-thio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, 5-pentynyluracil and 2,6-diaminopurine. The use of uracil as a substitute base for thymine in deoxyribonucleic acid (hereinafter referred to as "dU") is considered to be an "analogous" form of pyrimidine in this invention.

The oligonucleotides of polynucleotide decoys of the invention may contain analogous forms of ribose or deoxyribose sugars that are generally known in the art. An exemplary, but not exhaustive list includes 2' substituted sugars such as 2'—O-methyl-, 2'—O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and a basic nucleoside analogs such as methyl riboside.

Although the conventional sugars and bases may be used in applying the methods of the invention, substitution of analogous forms of sugars, purines and pyrimidines can be advantageous in designing the final product, as can alternative backbone structures like a polyamide backbone.

In addition the polynucleotide decoys of the invention may be comprised of short (the equivalent of up to 3 nucleotides in length) "spacer compounds" which duplicate the length and spacial geometry of a nucleotide, but do not engage in Watson-Crick-type binding with other nucleotides, and are not subject to cleavage by endonucleases. The various oligonucleotides which comprise the polynucleotide decoys (I, P$_1$, P$_2$, C$_1$, and C$_2$) of the invention are considered to encompass oligonucleotides in which up to about 3 nucleotides are replaced with one or more of the spacer compounds that are known in the art. Further, such replacements may be used to overcome the sensitivity of a decoy of the invention to particular endonucleases. If, for example, the stability of a particular decoy of the invention were found to be compromised by the cleavage of a particular endonuclease of a target cell, one or more of the nucleotides at the cleavage site could be replaced by a spacer compound.

However, the polynucleotide decoys of the invention are preferably comprised of greater than 50% conventional deoxyribose nucleotides, and most preferably greater than 90% conventional deoxyribose nucleotides.

The polynucleotide decoy sequences of the invention may be prepared by any known method, including synthetic, recombinant, ex vivo generation, or a combination thereof, as well as utilizing any purification methods known in the art.

The invention embodies nucleic acids comprising a linear polynucleotide decoy of the invention. The nucleic acids of the invention include expression vectors, amplification vectors, and PCR-suitable nucleic acids. In addition, the invention embodies amplification vectors, which comprise a decoy of the invention, and an origin of replication. Preferably, such amplification vectors further comprise restriction endonuclease sites flanking the decoy, so as to facilitate cleavage and purification of the decoy from the remainder of the amplification vector, and a selectable marker, so as to facilitate amplification of the amplification vector. Most preferably, the restriction endonuclease sites in the amplification vector are situated such that cleavage at those site would result in no other amplification vector fragments of a similar size.

Thus, such an amplification vector may be transfected into a host cell compatible with the origin of replication of said amplification vector, wherein the host cell is a prokaryotic or eukaryotic cell, preferably a mammalian, insect, yeast, or bacterial cell, most preferably an *Escherichia coli* cell. The resulting transfected host cells may be grown by culture methods known in the art, preferably under selection compatible with the selectable marker (e.g., antibiotics). The amplification vectors can be isolated and purified by methods known in the art (e.g., standard plasmid prep procedures). The decoy of the invention can be cleaved with restriction enzymes that specifically cleave at the restriction endonuclease sites flanking the decoy, and the double-stranded decoy fragment purified by techniques known in the art, including gel electrophoresis. Finally the decoy of the invention can be purified from its complementary fragment by repeatedly heating the double stranded decoy fragments, and allowing them to partially cool while passing them through a column designed to bind regions of the complementary non-decoy strand.

Alternatively linear polynucleotides comprising a decoy of the invention may be amplified by PCR. The PCR method is well known in the art and described in, e.g., U.S. Pat. Nos. 4,683,195 and 4,683,202 and Saiki, R. K., et al., *Science* (1988) 239:487–491, and European patent applications 86302298.4, 86302299.2 and 87300203.4, as well as *Methods in Enzymology* (1987) 155:335–350. The amplified DNA may then be recovered, in a single-stranded or dumbbell conformation, using conventional techniques, as well as those described above for decoys derived from amplification vectors.

The polynucleotide decoys of the invention can also be derivatized in various ways. The decoys can be derivatized by attaching a nuclear localization signal to it to improve targeted delivery to the nucleus. One well-characterized nuclear localization signal is the heptapeptide PKKKRKV (pro-lys-lys-lys-arg-lys-val)(SEQ ID NO:13). Preferably, in the case of polynucleotide decoys in the form of a closed circle, the nuclear localization signal is attached via a modified loop nucleotide or spacer that forms a branching structure.

Also, if the polynucleotide decoy is to be used for separation of transcription factors, one or more of the oligonucleotides of the decoy may be derivatized to a solid support to permit chromatographic separation. If the decoy is to be used to label the target transcriptional factor or otherwise attach a detectable moiety to this target, the oligonucleotide of the decoy will be derivatized to include a radionuclide, a fluorescent molecule, a chromophore or the like.

If it is to be used in vivo, the polynucleotide decoy of the invention may be derivatized to include ligands and/or delivery vehicles which provide dispersion through the blood, targeting to specific cell types, or permit easier transit of cellular barriers. Thus, the polynucleotide decoys of the invention may be linked or combined with any targeting or delivery agent known in the art, including but not limited to, cell penetration enhancers, lipofectin, liposomes, dendrimers, DNA intercalators, and nanoparticles. In particular, nanoparticles for use in the delivery of the polynucleotide decoys of the invention are particles of less than about 50 nanometers diameter, nontoxic, non-antigenic, and comprised of albumin and surfactant, or iron as in the nanoparticle particle technology of SynGenix. In general the delivery vehicles used to target the polynucleotide decoys of the invention may further comprise any cell specific or general targeting agents known in the art, and will have a specific trapping efficiency to the target cells or organs of from about 5 to about 35%.

The polynucleotide decoys of the invention may be used ex vivo in a method of obtaining MHC-II-depleted cells from target cells. The cells are created by incubation of the target cell with one or more of the above-described decoys under standard conditions for uptake of nucleic acids, including electroporation or lipofection. In practicing an ex vivo method of treating cells or organs, the concentration of decoys of the invention in a solution prepare to treat target cells or organs is from about 0.1 to about 100 $\mu$M, preferably 0.5 to 50 $\mu$M, most preferably from 1 to 10 $\mu$M.

Alternatively, the oligonucleotides can be modified or co-administered for targeted delivery to the nucleus. Improved oligonucleotide stability is expected in the nucleus due to: (1) lower levels of DNases and RNases; and (2) higher oligonucleotide concentrations due to lower total volume.

Alternatively, the decoys of the invention can be covalently bonded to biotin to form a biotin-decoy prodrug by methods known in the art, and co-administered with a receptor ligand bound to avidin or receptor specific antibody bound to avidin, wherein the receptor is capable of causing uptake of the resulting decoy-biotin-avidin complex into the cells. Receptors that cause uptake are known to those of skill in the art.

Any transplantable cell type is a potential target cell for this invention. Preferably, the target cell is selected from corneal endothelial cells, thyroid cells, parathyroid cells, brain cells, adrenal gland cells, bone marrow cells, pancreatic islet cells, hepatic cells, lymphoid cells, fibroblasts, epithelial cells, chondrocytes, endocrine cells, renal cells, cardiac muscle cells, keratinocytes, and hair follicle cells. Most preferably, the target cell is selected from corneal endothelial cells, thyroid cells, parathyroid cells, brain cells, adrenal gland cells, bone marrow cells, pancreatic islet cells keratinocytes, and hepatic cells.

In another aspect of this invention, the above-described decoys may be incorporated into a vector through methods well known in the art, and then inserted into the target cell via standard techniques such as electroporation, lipofection, or calcium phosphate or calcium salt mediation. In this fashion, the desired oligonucleotides can be produced in situ by the vector. When using an expression vector, the target cell will continue to express an RNA version of a decoy of the invention for at least a period of time following transplant.

Also, this invention is applicable to the field of solid organ transplants. Organs are normally perfused ex vivo prior to transplantation. By adding an amount of the above-described oligonucleotides to the perfusion medium, MHC-II-depleted cells can be created from perfusion-accessible cells in the organ to create an MHC-II-depleted organ useful in solid organ transplants. Any transplantable organ is a potential target organ for this invention. Preferably the target organ is selected from the group consisting of heart, liver, kidney, adrenal cortex, lung, intestine, pancreas, cornea and skin. Most preferably, the target organ is selected from the group consisting of heart, kidney, liver, cornea, and skin.

Finally, local administration of the polynucleotide decoys directly into the transplanted organ within several days after the transplant is within the scope of this invention. Also, sustained releases of the of these drugs are also contemplated.

As described above the polynucleotide decoys of this invention are useful in creating the MHC-II-depleted cells of this invention. These cells are then directly transplanted to an individual. For the purposes of the invention, an individual, treated with the cells or decoys of the invention, can be any animal, preferably any mammal, most preferably a human.

The polynucleotide decoys of this invention are also useful in treating autoimmune diseases characterized by dysfunctional or aberrant expression of an MHC class II antigen. The autoimmune diseases characterized by dysfunctional or aberrant expression of an MHC class II antigen include, but are not limited to, glomerulonephritis, thyroiditis, pancreatitis, rheumatoid arthritis, and primary biliary cirrhosis. In such a case, the oligonucleotides described herein may be administered systemically in an amount sufficient to inhibit expression of an MHC class II antigen, as measured by the techniques described herein.

As Reith et al. (1994) *Mol. and Cell. Biol.* 14: 1230–1244 note, RF-X1 is a transcription factor that was initially cloned by virtue of its affinity for the X-box motif, a conserved cis-acting regulatory element present in the promoters of all MHC class II genes from all species examined. RF-X was subsequently also found to bind with high affinity to the inverted repeats known as enhanced factor C (EF-C) sites, which are cis-acting regulatory elements present in the enhancers of several unrelated viruses, including hepatitis B virus (HBV), polyomavirus, and cytomegalovirus (CMV). Among these EF-C sites, the functional importance of the site in the HBV enhancer (EnhI) has been clearly demonstrated in several studies, including Dikstein et al. (1990) *Mol. Cell. Biol.* 10: 3683–3689, Garcia et al. (1993) *J. Virol.* 67: 3940–3950, Guo et al. (1991) *J. Viol.* 65: 6686–6692, Ostapchuk et al. (1989) *Mol. Cell. Biol.* 9:2787–2797, Siegrist et al. (1993) *Mol. Cell. Biol.* 13: 6375–6384, and Trujillo et al. (1991) *Proc. Natl. Acad. Sci. -U.S.A.* 88: 3797–3801. Of particular interest, RF-X1 specific antisense oligonucleotides have been shown to inhibit expression of the hepatitis B surface antigen gene, which is under the control of EnhI. In addition in a transient-transfection assays, RF-X1 was shown to be a potent transactivator of EnhI in vivo (Siegrist et al. (1993) *Mol. Cell. Biol.* 13: 6375–6384).

Thus, the invention embodies methods of treating an individual infected with viruses, which contain EF-C sites in their gene regulator elements (e.g., in enhancers or near transcription initiation sites), said methods of treatment comprising the systemic administration of a polynucleotide decoy of the invention to that individual. The viruses, which contain EF-C sites in their gene regulator elements may be determined by the methods described by Reith et al. (1994) *Mol. and Cell. Biol.* 14: 1230–1244. Such viruses include, for example, hepatitis B and cytomegalovirus.

In the case of treating an individual infected with hepatitis B virus, the decoy of the invention is administered in an amount sufficient to inhibit expression of hepatitis B surface antigen, antibody-based assays for measuring the levels of hepatitis B surface antigen are known in the art. In the case of treating an individual infected with cytomegalovirus, the method comprises administering to that individual a polynucleotide decoy of the invention in an amount sufficient to inhibit RF-X binding to the enhanced factor C sites of the cytomegalovirus genome. Appropriate assays for measuring the RF-X binding to cytomegalovirus EF-C sites can be developed by replacing the X-box sequences in the Gel shift assay and Cat assays of Examples 8 and 9, with cytomegalovirus EF-C sites, and cytomegalovirus enhancers respectively. The use of the decoys of the invention for the treatment of cytomegalovirus is particularly directed to the prevention of the onset of cytomegalovirus retinitis in HIV infected patients. Thus, the decoys of the invention can be used as a prophylaxis in any HIV infected patient. The HIV-induced suppression of the immune system is thought to allow the normally benign cytomegalovirus to cross the blood-retina barrier, infecting the choroid and retinal tissues, and cause blindness.

Under physiological conditions, the polynucleotide decoys of the invention, whether linear or covalently closed, are considered to exist in a dumbbell conformation. Thus, while all of the polynucleotide decoys of the present invention maintain some sequence homology with the X box of MHC-II, the dumbbell conformation should prevent these polynucleotide decoys from being capable of binding to any transplantation antigen nucleotide sequence.

The mechanism by which the polynucleotide decoys of the invention interfere with or inhibit the production of one or more MHC-II antigens is not always established, and is not a necessary part of the invention. The polynucleotide decoys of the invention are characterized structurally and by their ability to bind to RF-X transcription factors, regardless of the specific mechanisms of RF-X binding, or the mechanism of the effect thereof.

Described below are examples of the present invention which are provided for illustrative purposes, and not to limit the scope of the present invention. In light of the disclosure, numerous embodiments within the scope of the claims will be apparent to those of ordinary skill in the art.

EXAMPLES

Example 1
Synthesis of a Dolynucleotide decoy

A linear, HPLC purified 42-mer oligonucleotide was purchased from Keystone Labs (Menlo Park, Calif.). The sequence of the linear 42-mer oligonucleotide is as follows:

DNA was visualized on a silica gel plate using UV light. The band of interest was excised, "crushed and soaked" in detergent buffer, and purified through a Sep-pak $C_{18}$ reverse-phase column.

A polynucleotide decoy synthesized as described above in Example 1 was run on a 15% polyacrylamide gel. FIG. 1 shows a print from a minigel, visualized with ethidium bromide on an ultraviolet illuminator. The polynucleotide decoy (Lane 5) migrated faster than the unligated linear 42-mer (Lane 8).

Example 3
Proof of Synthesis & Resistance to Nucleases

To demonstrate that the product resulting from the synthesis was indeed the polynucleotide decoy, it was subjected to the following enzymes, each of which is expected to degrade only non-ligated material:

(a) Klenow fragment from *E. coli* DNA polymerase, a 3' to 5' exonuclease;

(b) Shrimp alkaline phosphatase, a 5'-dephosphorylating agent; and (c) Nuclease S1, a nuclease that is relatively single-strand specific at high salt and low enzyme conditions.

Figure 2:
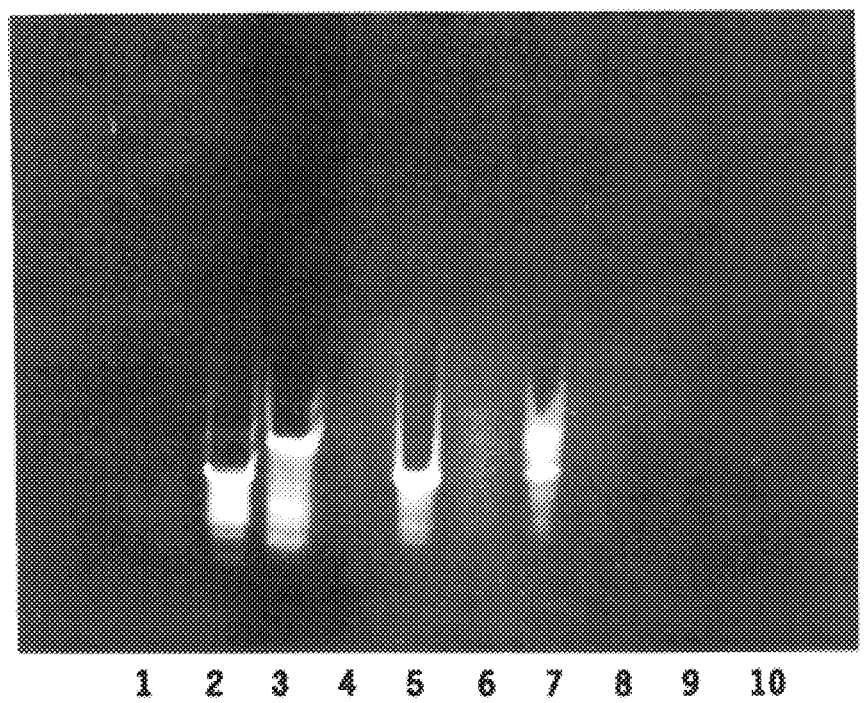
Figure 3:
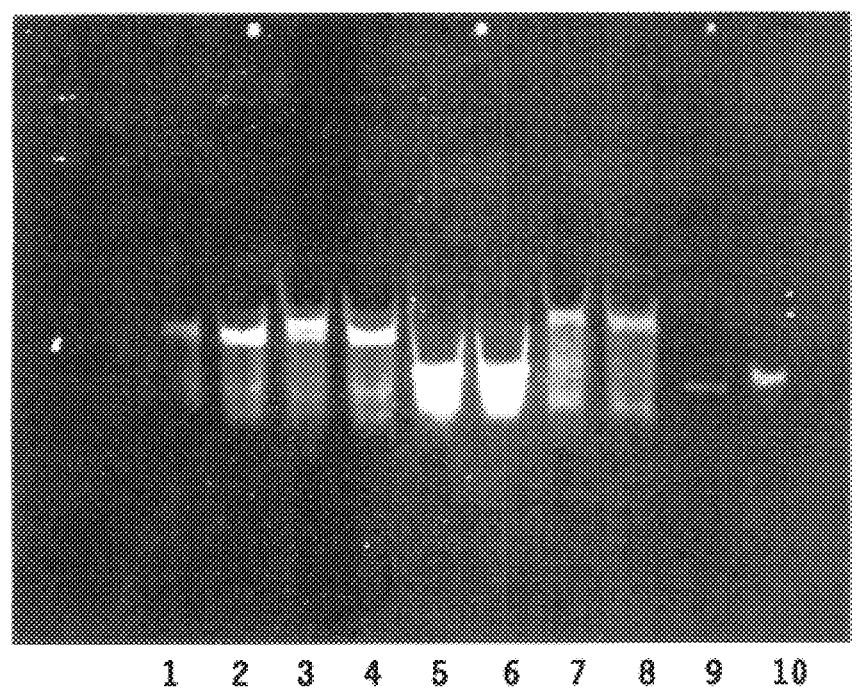
Figure 4:
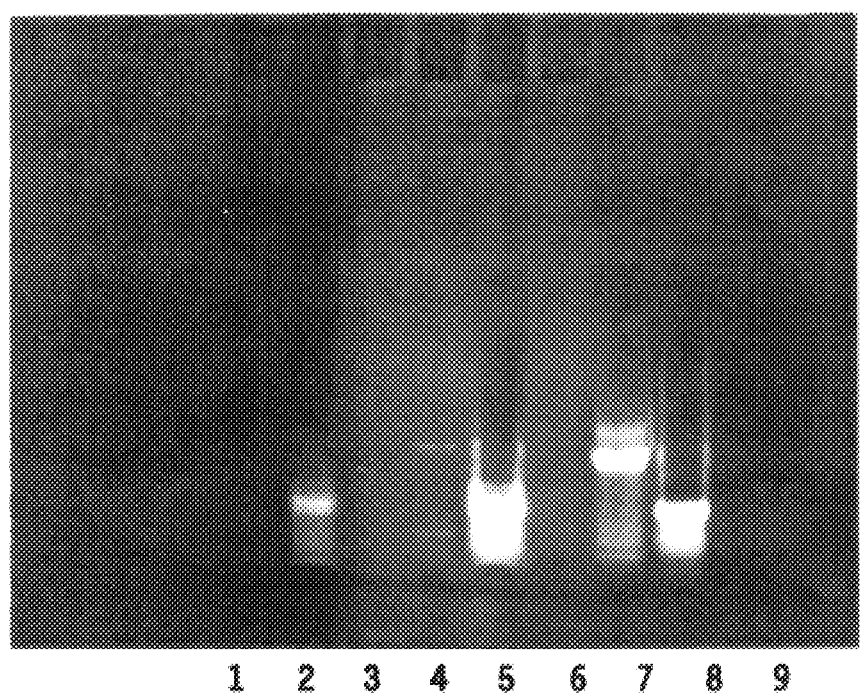

FIGS. 2–4 are prints from minigels showing results from the enzymatic treatments, visualized with ethidium bromide on an ultraviolet illuminator.

Klenow fragment acts as a 3' to 5' exonuclease, degrading from free 3'-hydroxyl termini. The polynucleotide decoy should be resistant to this activity compared to linear sequence. FIG. 3 shows migration of the untreated polynucleotide decoy (Lane 2) and the untreated linear oligonucleotide (Lane 3); after 8 hours of enzyme treatment, the linear oligonucleotide (Lane 4) is completely degraded, while the polynucleotide decoy (Lane 5) migrates as the untreated control, showing that it is resistant to exonuclease; after 12 hours of enzyme treatment, the linear oligonucleotide (Lane 8) has completely degraded, while polynucleotide decoy (Lane 7) has begun to degrade.

Shrimp alkaline phosphatase cleaves off phosphate from the 5' end. The polynucleotide decoy should be resistant to this treatment, as it has no free 5' phosphate. FIG. 3 shows identical migration of the treated polynucleotide decoy (Lane 6) and the untreated polynucleotide decoy (Lane 5); treated linear oligonucleotide (Lane 2), linear phosphorylated oligonucleotide (Lane 3), and treated linear phosphorylated oligonucleotide (Lane 4) are all shortened.

S1 nuclease degrades single strand DNA more rapidly than double stranded DNA under reaction conditions of high salt and low enzyme concentration. The polynucleotide decoy should be comparatively resistant to the treatment, and the middle portion is base paired. FIG. 4 shows migration of untreated polynucleotide decoy (Lane 8) and untreated oligonucleotide (Lane 7); after 5 minutes of treatment linear oligonucleotide (Lane 4) has been degraded to a great extent, while the polynucleotide decoy is still present

5'-GCTAGGGGTTTTTCCCCTAGCAACAGATGTTTTTCATCTGTT-3' (SEQ ID NO:14)

The 42-mer oligonucleotide was phosphorylated with T4 polynucleotide kinase, then heated to inactivate the kinase, and subsequently allowed to anneal by cooling slowly to room temperature. It was then ligated with T4 DNA ligase.

Example 2
Purification of a polynucleotide decoy

For large scale purification, the polynucleotide decoy (about 20 μg per lane) was run on a polyacrylamide gel. The (Lane 5); after 20 minutes of treatment the oligonucleotide has been completely degraded (Lane 1), while the polynucleotide decoy is still present (Lane 2).

Example 4
Electrophoretic Mobility Shift Assays ("EMSA")

Preliminary in vitro binding experiments (EMSA) demonstrated specific binding between the polynucleotide decoy prepared in Example 1 and RF-X (of which a sample was obtained from Dr. B. M. Peterlin, Medicine; Microbiology and Immunology, University of California, San Francisco). In such a gel shift assay, the RF-X-polynucleotide decoy complex should show reduced mobility as compared to RF-X alone. Initial studies involved competition for RF-X by the polynucleotide decoy of the invention and by a radiolabeled, double-stranded X-box probe.

The binding assays were performed generally as described in Hasegawa et al. (1991), *Nucleic Acids Res.*, Vol. 19(6), pp. 1243–9, under the following conditions. The samples were preincubated for 10 minutes on ice with: binding buffer, polydIdC, RF-X (from rabbit reticulocyte lysate), and a competitor (one of: polynucleotide decoy, X-box probe, non-specific double-stranded 10-mer or 20-mer) or no competitor. Following preincubation, $^{32}$p, end-labeled, double-stranded DRA X-box probe (~30-mer) was added, and allowed to incubate 20 minutes on ice.

Figure 5:
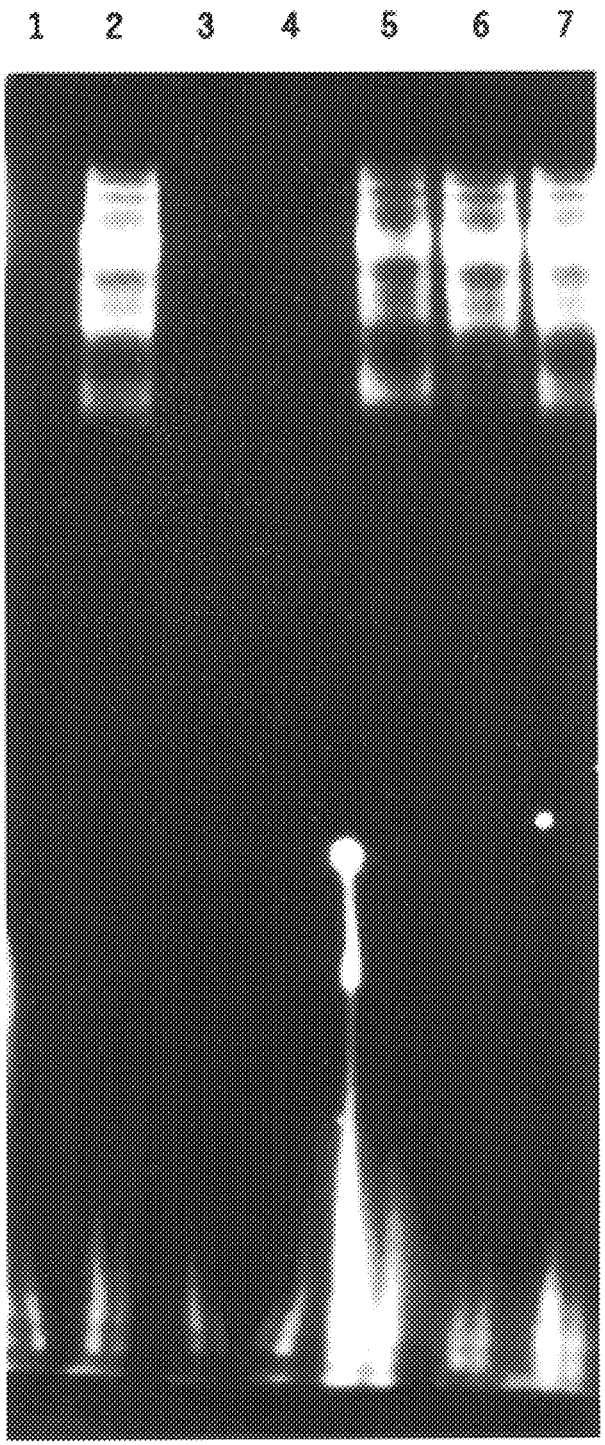
FIG. 5 is a half-tone reproduction from a gel from an electrophoretic mobility shift assay of RF-X incubated with various nucleotides at various concentrations.

The resulting reactants were run on a 5% native polyacrylamide gel (TBE). FIG. 5 is an autoradiograph of a gel showing the results for RF-X preincubated with: (Lane 1) double strand X box probe (100 excess compared to $^{32}$P-labelled probe); (Lane 2) control (no DNA added); (Lane 3) polynucleotide decoy (100 fold excess); (Lane 4) polynucleotide decoy (200 fold excess); (Lane 5) non-specific double-stranded 10-mer (500 fold excess); (Lane 6) non-specific double-stranded 10-mer (500 fold excess); (Lane 7) control (no DNA added). The $^{32}$P-labeled DRA X-box probe was unable to compete off the polynucleotide decoy from RF-X at selected concentrations.

Example 5
Activity of the Polynucleotide Decoys in Cells is Measured by Flow Cytometry:

The effect of the polynucleotide decoy on HLA II DRα gene expression are determined using fluorescence flow cytometry. Fluorescently tagged antibodies are used for fluorescence-activated cell sorting ("FACS") analysis of HLA II DRα cell surface expression. An RNAse protection assay is used to determine the levels of HLA II DRα mRNA. The polynucleotide decoy may inhibit constitutively expressed HLA or inducible HLA (for example, γ-IFN inducible), or both inducible and constitutively expressed HLA. Many different human cell lines are used to assay for specific inhibition; as noted above, for example, the B-lymphoma cell line Raji constitutively expresses HLA class II; the HeLa S3 cell line is inducible with γ-IFN.

Example 6
Method for Synthesis of Polynucleotide Decoys:

Oligonucleotides. Oligonucleotides (oligos) were purchased from either Keystone Laboratories (Menlo Park, Calif.) or Oligos Etc. (Wilsonville, Oreg.). Synthesis of polynucleotide decoys from linear oligos involves phosphorylation followed by ligation (Wemmer et al. (1985), *Nucl. Acid. Res.*, Vol. 13(23), pp. 8611–21; Erie et al. (1987), *Biochemistry*, Vol. 26(22), pp. 7150–9; Erie et al. (1989), *Biochemistry*, Vol. 28(1), pp. 268–73; and Chu et al. (1991) *Nucl. Acids Res.* 19: 6958.

Oligonucleotides used to make polynucleotide decoys. Internal double stranded sequences underlined.

5 T oligos

| | | |
|---|---|---|
| 42 mer: | 5'-CTAGGGGTTTTTCCCCTAGCAACAGATGTTTTTCATCTGTTG-3' | (SEQ ID NO:9) |
| 38 mer: | 5'-TGCTAGGTTTTTCCTAGCAACAGATGTTTTTCATCTGT-3' | (SEQ ID NO:12) |

4 T oligos, all 40 mers

| | | |
|---|---|---|
| RF-X-2: | 5'-GACTGGGTTTTCCCAGTCCATACGAAGTTTTCTTCGTATG-3' | (SEQ ID NO:7) |
| RF-X: | 5'-CTAGGGGTTTTCCCCTAGCAACAGATGTTTTCATCTGTTG-3' | (SEQ ID NO:6) |
| NF-kB: | 5'-TCCCTTGGTTTTCCAAGGGACTTTCCGCTTTTGCGGAAAG-3' | (SEQ ID NO:21) |
| M6 mutant: | 5'-TATACGGGTTTTCCCGTATACCACTCTGTTTTCAGAGTGG-3' | (SEQ ID NO:15) |
| kB mutant: | 5'-TGAGTTGGTTTTCCAACTCACTTTCCGCTTTTGCGGAAAG-3' | (SEQ ID NO:16) |
| kB: | 5'-TCCCTTGGTTTTCCAAGGGACTTTCCGCTTTTGCGGAAAG-3' | (SEQ ID NO:17) |
| hlyn site: | 5'-TAACAACTTTTGTTGTTATAGTAACTTTTGTTACTA-3' | (SEQ ID NO:18) |

Annealed Oligos:

| | | |
|---|---|---|
| Top Strand | 5'-CCCCTAGCAACAGATG | (SEQ ID NO:11) |
| Bottom Strand | 3'-GGGGATCGTTGTCTAC | (SEQ ID NO:2) |

Phosphorylation. 100 nmol of oligo was phosphorylated with T4 polynucleotide kinase (USB), 5 units/nmol, 2 mM ATP (Mg salt), 500 mM Tris HCl pH 7.6, 10 mM MgCl$_2$, 10 mM 2-mercaptoethanol at 37° C. After 1 hour additional ATP and 1 unit/nmol T4 polynucleotide kinase were added; the reaction was incubated for 1 hour at 37° C. A final aliquot of ATP and T4 polynucleotide kinase was added, and the reaction was incubated for 24 hours at 37° C.

Ligation. The phosphorylated oligo reaction mixture was heated to 80°–90° C. for 10 minutes to inactivate the kinase and to remove secondary structure. It was cooled slowly to room temperature (3 hours) to facilitate intramolecular annealing. Ligation was performed with a 3-fold molar excess of T4 DNA ligase (USB), 5% polyethylene glycol, 66 mM Tris HCl pH 7.6, 6.6 mM $MgCl_2$, 10 mM DTT, and 66 mM ATP at 16° C. for 48 hours. The sample was frozen at −20° C.

Nuclease Reactions. The reaction product (at various stages) was tested for resistance to various nucleases: shrimp alkaline phosphatase (USB), Klenow fragment of *E. coli* (Worthington), and S1 nuclease (Worthington), and Mae I (Boehringer Mannheim).

Purification. Ligated material was separated from unreacted material on a 15% denaturing polyacrylamide gel. For the gel shift assay, ligated products were sliced from the gel and transferred to a microfuge tube, then crushed and soaked (in TE, pH 7.8) overnight in a 37° C. shaking water bath. It was then Speed Vac'd (Savant) until dry. The decoy was then reconstituted to a concentration of 10 pmol/ml for the gel shift assay. For cell studies, oligos were eluted from gel slices using BioRad's Model 422 electro-eluter, then ethanol precipitated.

Often these decoys are analyzed on polyacrylamide gels to determine purity (i.e., shorter failed sequences) or to check for secondary structure (such as hairpins or dumbbells). Two non-radioactive stains are used to visualize such decoys on polyacrylamide gels: ethidium bromide and methylene blue. Methylene blue has been touted as an inexpensive, non-toxic alternative to ethidium bromide (Young-Sharp, D. and R. Kumar. (1989) *Technique* 1(3): 183–187), staining both single- and double-stranded oligos with equal intensity. For most purposes methylene blue is adequate for staining short oligos. Ethidium bromide has an advantage when looking for oligo secondary structure because it preferentially stains double-stranded DNA. However, ethidium bromide is inefficient for visualizing short single-stranded oligos at low concentrations. By using these dyes sequentially we can both detect single- and double-stranded oligos at low concentrations and differentiate between them.

Table 1 illustrates the minimum amounts of single- and double-stranded oligos of variable sequences/lengths detectable using the 2 different dyes. Similar results were obtained using phosphorothioate and 3'-amino-modified oligos. Single-stranded oligos were analyzed on denaturing 12% polyacrylamide gels (Sambrook, J., E. F. Fritsch and T.

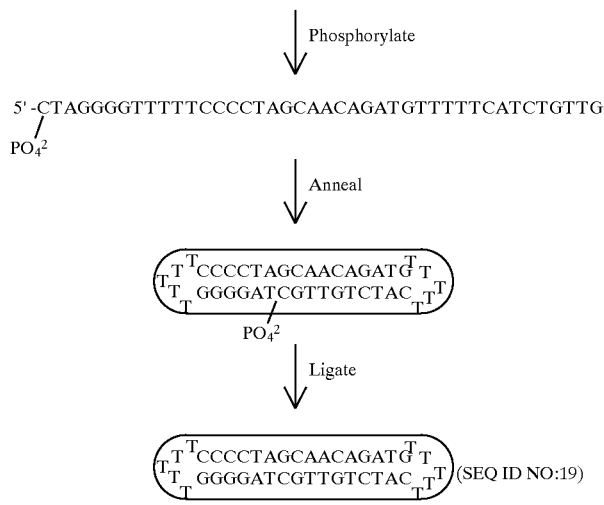

Results of Synthesis. Successful synthesis was determined by analyzing the products on a polyacrylamide gel and subjecting the products to various nucleases. Nuclease reactions. The RF-X polynucleotide decoy was found to be more resistant to the exonuclitic action of the Klenow fragment compared to the non-ligated sequence. The polynucleotide decoy was degraded more slowly by S1 nuclease (a relatively single-strand specific nuclease) compared to the non-ligated sequence. The polynucleotide decoy was completely resistant to shrimp alkaline phosphatase. In addition, the polynucleotide decoy was cleaved more readily into 2 segments by the restriction enzyme Mae I, which recognizes the double-strand sequence 5'-CTAG found in the polynucleotide decoy. All nuclease reactions were analyzed using gel electrophoresis as described in Example 2.

Example 7
Staining to Distinguish Between Covalently Closed Polynucleotide Decoys & Single-stranded Oligonucleotides Maniatis. (1989) *Molecular Cloning: A Laboratory Manual*. Cold Spring Harbor Laboratory Press. Plainview, N.Y.) (5 g urea, 4.69 ml 30% acrylamide solution, 1.88 ml 5×TBE, 56 ml 10% ammonium persulfate, 3.5 ml TEMED, and 0.5 ml of 10 mg/ml ethidium bromide solution) and loaded with formamide-containing sample buffer. Double-stranded oligos were analyzed on non-denaturing 20% gels (Sambrook, J., E. F. Fritsch and T. Maniatis. (1989) *Molecular Cloning: A Laboratory Manual*. Cold Spring Harbor Laboratory Press. Plainview, N.Y.) (6.66 ml 30% acrylamide solution, 2 ml 5×TBE, 1.27 ml water, 56 ml 10% ammonium persulfate, 3.5 ml TEMED, and 0.5 ml of 10 mg/ml ethidium bromide solution) and loaded with glycerol-containing sample buffer. Cassettes (1 mm), 10-well combs, and the Xcell Mini-cell system from Novex (San Diego, Calif.) were used. Running buffer (1.25×TBE) included 0.5 mg/ml ethidium bromide. After 1.5 hours of electrophoresis at 150 V (~15 mamp), the gel was removed from the cassette and photographed in the dark using a Polaroid camera and ultraviolet light source.

Immediately after photography, the gel was stained for approximately 5 minutes using 0.02% methylene blue. The gel was destained with warm water (2–5 washes) until background was clear, then photographed on top of a fluorescent light box.

We have used this sequential staining technique to distinguish (on a 19% denaturing acrylamide gel) products from reactants in a ligation reaction (Chu, B. C. and L. E. Orgel. (1991) *Nucl. Acid. Res*. 19(24): 6958) where the reactant is a 42 mer single-stranded, intramolecularly annealing oligo and the product is a closed, double-stranded, dumbbell-shaped oligo of the same length. Although the molecular weights of the product and reactant are similar, they migrate at significantly distinct rates due to their structural difference (Chu, B. C. and L. E. Orgel. (1991) *Nucl. Acid. Res*. 19(24): 6958). This technique has also been successfully used to analyze ligation reactions involving oligos with different sequences and lengths. Ethidium bromide helps to distinguish between our reactants (single-stranded) and products (double-stranded) while methylene blue may allow quantification of percent yield for the reaction. We are thus able to obtain more information from gels stained with two consecutive agents rather than just one. The polynucleotide decoys used in the gels:

Lane 1. 42mer product:

$_T T^T$CCCCTAGCAACAGAT$G^T$T
$T_T$ GGGGATCGTTGTCTAC$_T$T (SEQ ID NO:5)

Lane 2. 42mer reactant:

5'-CTAGGGGTTTTTCCCCTAGCAACAGATGTTTTTCATCTGTTG-3' (SEQ ID NO:19)

transcription factors. The competition assay was able to test whether a decoy was able to compete with a radiolabeled control sequence, usually the double-stranded extended X-box, also referred to as "AX", for binding to RF-X. RF-X transcription factors were obtained from a nuclear extracts and incubated with the polynucleotide decoy of interest. In the case of the competition assay the competing oligo was added to see if it could displace the other oligo from RF-X. The mixtures were then run on a gel, and radioactive bands were detectable by autoradiography.

Detailed Methods

Nuclear Extracts

Nuclear extracts, containing RF-X transcription factors, were obtained from Raji cells using the method of Ohlsson et al. (1986), *Cell*, Vol. 45(1), pp. 35–44.

Direct Binding Assay Conditions

The following mixture was made and incubated for 20 minutes on ice:

a. binding buffer (12 mM HEPES-KOH, 12% glycerol, 60 mM KCl, 5 mM $MgCl_2$, 0.12 mM EDTA, 0.3 mM DTT)

b. polydIdC (non-specific DNA competitor, 2 µg)

c. RF-X transcription factor from nuclear extract: ~3 µg

TABLE 1

Approximate amounts (mg) of oligonucleotide detectable with methylene blue and ethidium bromide.

|  | Approximate Amounts (mg) Detectable: | |
| --- | --- | --- |
|  | Methylene Blue | Ethidium Bromide |
| single-stranded 16mer<br>5'-CCCCTAGCAACAGATG-3' (SEQ ID NO: 1) | 0.05 | >10 |
| single-stranded 20mer<br>5'-GCCACGGAGCGAGACATCTC-3' (SEQ ID NO: 20) | 0.05 | >1 |
| single-stranded 40mer<br>5'-CTAGGGGTTTTCCCCTAGCAACAGATGTTTTCATCTGTTG-3' (SEQ ID NO: 6) | 0.05 | 0.01 |
| double-stranded 16 bp<br>5'-CCCCTAGCAACAGATG-3' (SEQ ID NO: 1)<br>3'-GGGGATCGTTGTCTAC-5' | 0.05 | 0.1 |
| double-stranded 20 bp<br>5'-GCCACGGAGCGAGACATCTC-3' (SEQ ID NO: 21)<br>3'-CGGTGCCTCGCTCTGTAGAG-5' | 0.05 | 0.05 |
| 40mer decoy<br>(double-stranded 16 bp)<br><br>$_T T^T$CCCCTAGCAACAGATG$^T$T (SEQ ID NO: 23)<br>$T_T$-GGGGATCGTTGTCTAC$_T$T | 0.005–0.01 | 0.005–0.01 |

Example 8
Gel Shift Assays—Methods and Results

There were 2 types of gel shift assays performed: the direct binding assay and the competition assay. The direct binding assay was able to test whether or not a radiolabeled polynucleotide decoy was able to directly bind to RF-X d. test compound (DNA decoy, X-box probe=AX, or other nucleic acid of interest)

Competition Assay Conditions (similar to the assay performed by Hasegawa et al. (1991), *Nucleic Acids Res.*, Vol. 19(6), pp. 1243–9)

1. The following mixture was made and incubated for 10 minutes on ice:
   a. binding buffer (12 mM HEPES-KOH, 12% glycerol, 60 mM KCl, 5 mM MgCl$_2$, 0.12 mM EDTA, 0.3 mM DTT)
   b. polydIdC (non-specific DNA competitor, 2 µg)
   c. RF-X transcription factors from nuclear extract: ~3 µg
   d. competitor (polynucleotide decoy; or controls of X-box probe, non-specific double-stranded 10-mer, or nothing)
2. After the 10 minute incubation, $^{32}$p end-labeled, double-stranded DRA X-box probe (~50-mer) (the sequence of which is described by Hasegawa et al. (1991), *Nucleic Acids Res.*, Vol. 19(6), pp. 1243–9) was added and incubated for 30 minutes.

Gel: Run reaction mixtures on 5% native polyacrylamide gel; re-circulate 0.25×TBE buffer. Run time: ~2 hours (150–175 V, 200 Watts, 10 mAmp)

Autoradiograph: expose X-ray film O/N at −70° C.

Detailed Results:

When the Direct Binding Assay was performed, Lane 1 demonstrated RF-X transcription factor binding to the hot AX probe. Lane 2 demonstrated that the cold AX probe was able to compete off the hot AX probe (cold AX in a 30-fold excess). These 2 lanes served as controls for comparison with all lanes with test compounds. The 16 bp X-box, M6 decoy, unligated M6 decoy, RF-X-2 decoy, unligated RF-X-2 decoy, unligated RF-X decoy T5, and unligated κB mutant (lanes 3, 6, 7, 8, 9, and 12, respectively) demonstrated no measurable binding to the RF-X transcription factors. The RF-X decoy (lane 4) bound to RF-X, as did the unligated RF-X decoy (lane 5) and the RF-X decoy T5 (lane 10), but the latter 2 to a lesser degree.

When the Competition Assay was performed, Lane 1 exhibited RF-X transcription factor binding to the hot AX probe. For competition to occur, the competing oligo should "displace" the hot AX probe from the RF-X transcription factors. The oligos containing the core X-box sequence could compete with hot AX for binding to RF-X; cold AX (lane 2), unligated RF-X decoy (lanes 3, 4, 9), RF-X decoy (lanes 5, 6), RF-X decoy T5 (lane 7), and 16 bp X-box (lane 9). Lane 11, the κB mutant, did not compete, nor did a non-specific 20-mer oligo (lane 12).

Example 9
CAT Assays—Methods and Results

When Raji cells were transfected with pDRASCAT plasmid, basal CAT activity could be measured. When Raji cells are co-transfected with pDRASCAT and a decoy, we were able to measure the specific effect of the various decoys on the basal CAT activity. Decoys that diminished CAT activity were considered "active." "Inactive" oligos demonstrated little or no effect on CAT activity.

Detailed Methods

Cell culture. MHC Class II expressing Raji cells (ATCC COWL 86, a human Burkitt's lymphoma B-cell line) were grown in RPMI 1640 medium with fetal bovine serum (20%), penicillin (100 U/ml), streptomycin (100 µg/ml), and L-glutamine (292 µg/ml).

Plasmids. The plasmid PDRASCAT has been described previously (Tsang et al. (1990), *Mol. Cell. Biol.*, Vol. 10(2), pp. 711–719; and Voliva et al. (1992), *Mol. Cell. Biol.*, Vol. 12(5), pp. 2383–90). Briefly, it contains the DRA promoter from positions −150 to +31 linked to the CAT gene.

Transfections. 1×106 to 4×106 Raji cells (in ½ ml) were electroporated with 20 to 40 µg pDRASCAT plasmid, along with 10 µM of a test decoy (or no nucleic acid) using the Bio-Rad Gene pulsar® set at 300 V and 960 µF. After 10 minutes, the cells were transferred to 4.5 ml complete media.

CAT assays. Cells were harvested for CAT assays approximately 48 hours after electroporation. The polynucleotide decoys and other oligonucleotides were synthesized as described in Example 6. CAT assays were performed using the method of Neumann et al. (1987), *Biotechniques*, Vol. 5(5), pp. 444–447, which involves measurement of CAT by scintillation counting. Counts were directly proportional to CAT activity.

Detailed Results

For all figures, basal CAT activity (PDRASCAT plasmid transfected alone) shown by white bar, CAT activity in the presence of oligos shown by shaded bars. The shaded bars should be compared to the white bar in order to quantify the decreased CAT activity as a result of the addition of a decoy.

Figure 6A:
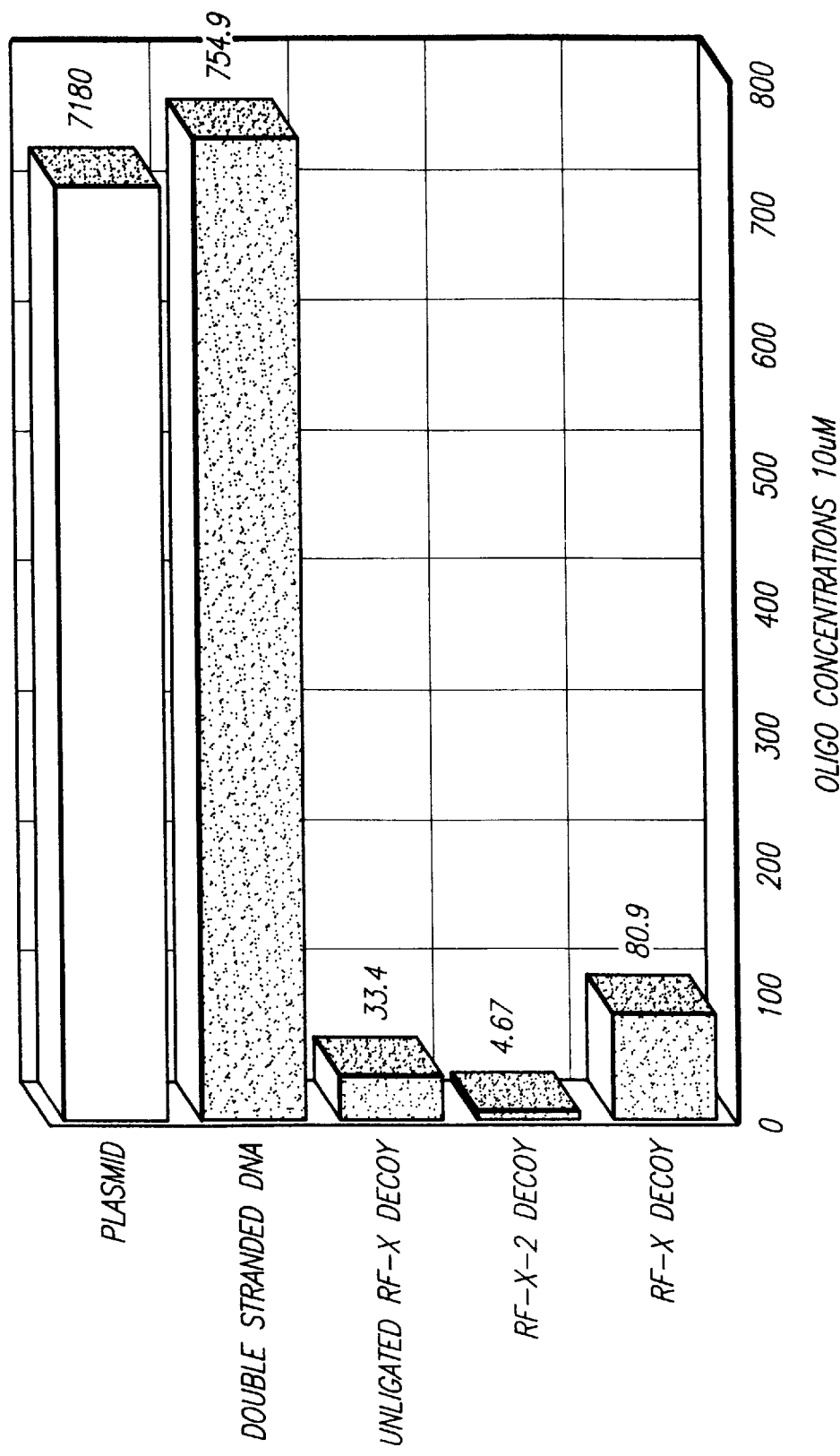
FIGS. 6 A–C are graphs summarizing the effects of various decoys and control sequences on the CAT activity of Raji cells transfected with the plasmid pDRASCAT which contains the DRA promoter from positions −150 to +31 linked to the CAT gene.

FIG. 6A (plasmid, ds DNA, unlig RF-X decoy, RF-X-2 decoy, RF-X decoy):

Doubled stranded X-box DNA demonstrated no effect on CAT activity. While unligated RF-X decoy, RF-X-2 decoy, and RF-X decoy all decrease CAT activity significantly.

Figure 6B:
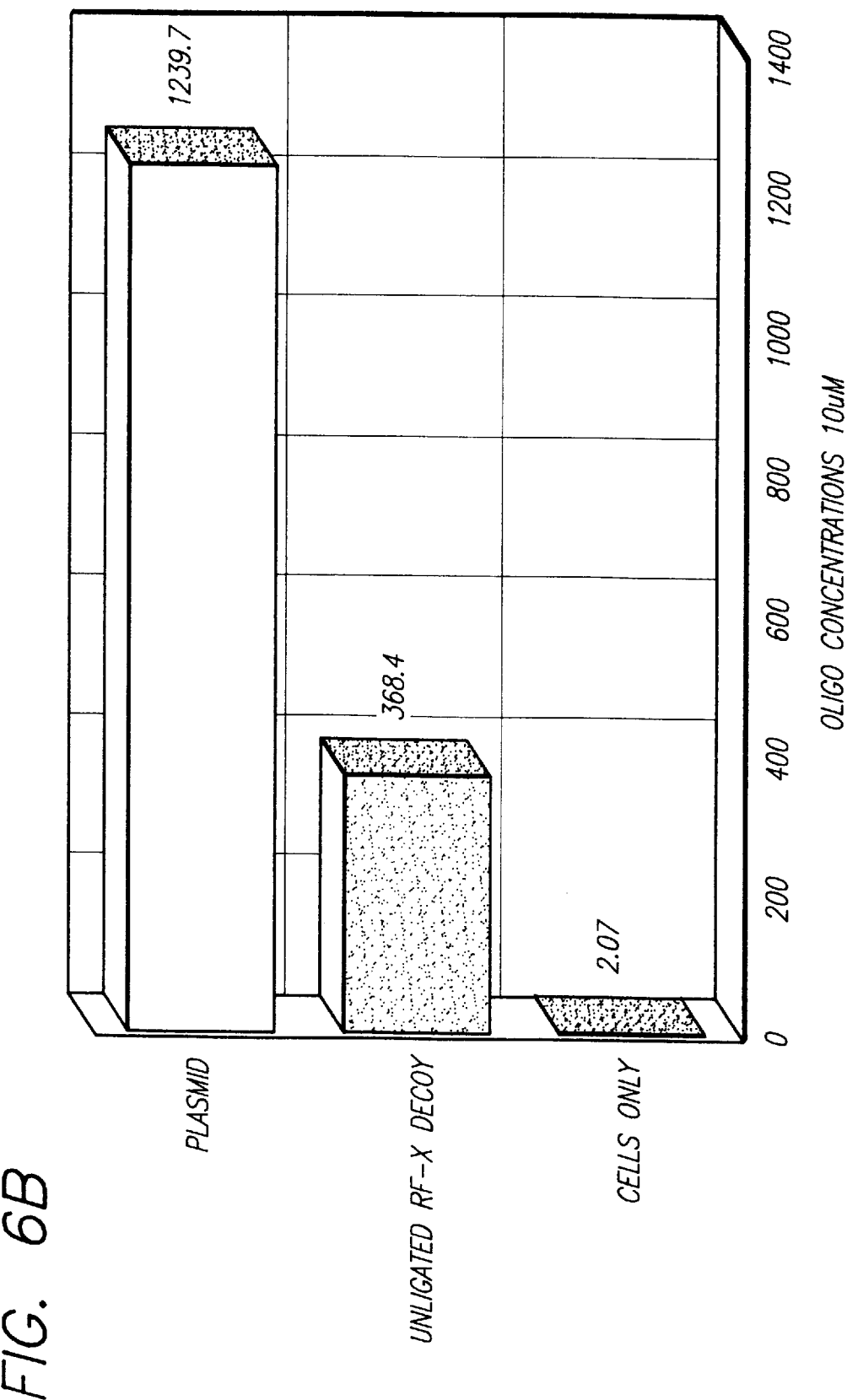

FIG. 6B (plasmid, unlig RF-X decoy, cells only):

Unligated RF-X decoy, again decreased CAT activity. When no plasmid is transfected (cells alone), Raji cells displayed minimal basal CAT activity, as expected. This "cells-alone" data point was generated as an internal control.

Figure 6C:
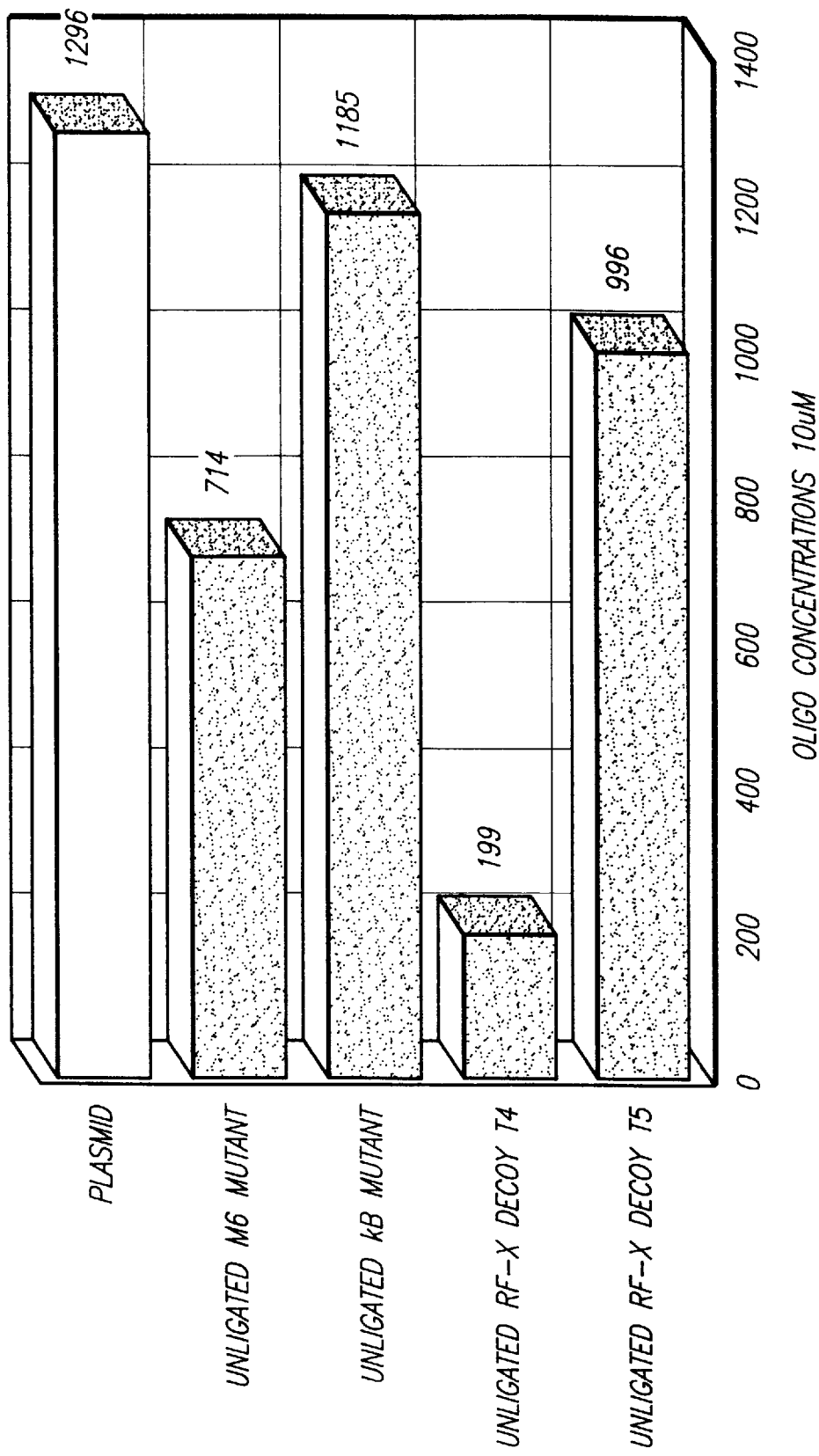
Figure 7:
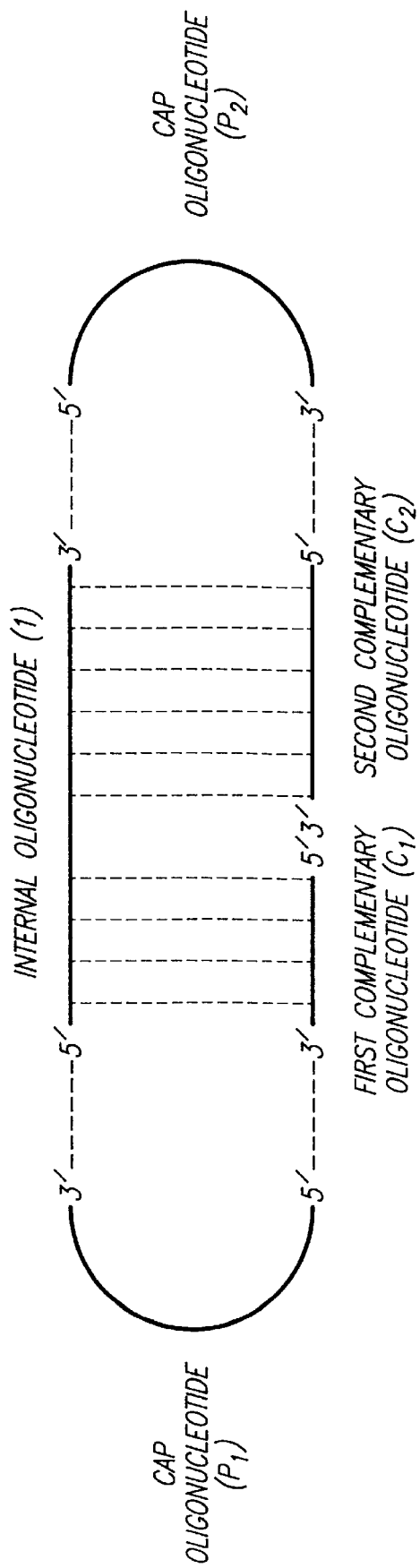
FIG. 7 is a schematic drawing of one embodiment of the polynucleotide decoy structure according to the invention.

FIG. 6C (plasmid, unlig M6 mutant, unlig κB mutant, unlig RF-X decoy T4, unlig RF-X decoy T5):

Only the unligated RF-X decoy T4 (4 T's in the loop) decreased CAT activity in this experiment. All other decoys were inactive.

Summary of Data for CAT Assays of Decoys

All oligos co-transfected (electroporated) with pDRAS-CAT plasmid unless otherwise indicated Active Decoy: Down-regulated pDRASCAT
  RF-X decoy
  unligated RF-X decoy
  RF-X-2 decoy
  unligated RF-X-2 decoy
  unligated κB decoy Inactive Decoys: No Significant Down-regulation of pDRASCAT
  double-stranded (preannealed) X-box, 16 bp
  unligated 5T loop RF-X decoy
  unligated M6 mutant decoy
  unligated κB mutant decoy
  passively administered unligated RF-X decoy

We claim:

1. A polynucleotide decoy comprising an oligonucleotide selected from the group consisting of:

(SEQ ID NO:6)
5'-CTAGGGGTTTTCCCCTAGCAACAGATGTTTTCATCTGTTG-3', (SEQ ID NO:7)
5'-GACTGGGTTTTCCCAGTCCATACGAAGTTTTCTTCGTATG-3', and (SEQ ID NO:11)
5'-TCCCTTGGTTTTCCAAGGGACTTTCCGCTTTTGCGGAAAG-3'.

wherein said polynucleotide decoy binds to an RF-X transcription factor.

2. A polynucleotide decoy according to claim 1, wherein the 3' end and the 5' end of said oligonucleotide are covalently linked.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 16 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:1:

CCCCTAGCAA CAGATG           16

( 2 ) INFORMATION FOR SEQ ID NO:2:

( i ) SEQUENCE CHARACTERISTICS:
      ( A ) LENGTH: 16 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:2:

CATCTGTTGC TAGGGG           16

( 2 ) INFORMATION FOR SEQ ID NO:3:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i x ) FEATURE:
      ( A ) NAME/KEY: misc_feature
      ( B ) LOCATION: group(1, 4, 9, 12)
      ( D ) OTHER INFORMATION: /note= "R represents a purine
          residue"

( i x ) FEATURE:
      ( A ) NAME/KEY: misc_feature
      ( B ) LOCATION: group(5, 6, 14)
      ( D ) OTHER INFORMATION: /note= "Y representsa pyrimidine
          residue"

( i x ) FEATURE:
      ( A ) NAME/KEY: misc_feature
      ( B ) LOCATION: group(3, 8, 11)
      ( D ) OTHER INFORMATION: /note= "Y* represents either a
          5-methyl cytosine or a thymidine residue"

( x i ) SEQUENCE DESCRIPTION: SEQ ID NO:3:

RTYRYYAYRG YRAY           14

( 2 ) INFORMATION FOR SEQ ID NO:4:

( i ) SEQUENCE CHARACTERISTICS:
      ( A ) LENGTH: 18 base pairs
      ( B ) TYPE: nucleic acid
      ( C ) STRANDEDNESS: double
      ( D ) TOPOLOGY: linear ( i x ) FEATURE:
      ( A ) NAME/KEY: misc_feature
      ( B ) LOCATION: group(1, 4, 6, 9, 10, 11, 12, 18)
      ( D ) OTHER INFORMATION: /note= "N represents any
          nucleotide"

( i x ) FEATURE:

(A) NAME/KEY: misc_feature
(B) LOCATION: group(3, 8)
(D) OTHER INFORMATION: /note= "Y* represents a nucleotide comprising a 5-methylated pyrimidine, preferably a 5-methyl cytosine or a thymidine deoxyribonucleotide"

(ix) FEATURE:
(A) NAME/KEY: misc_feature
(B) LOCATION: group(5, 14)
(D) OTHER INFORMATION: /note= "Y represents a nucleotide comprising a pyrimdine, preferably a cytosine or thymidine deoxyribonucleotide"

(ix) FEATURE:
(A) NAME/KEY: misc_feature
(B) LOCATION: group(7, 15, 16)
(D) OTHER INFORMATION: /note= "R represents a nucleotide comprising a purine, preferably an adenine or guanine deoxyribonucleotide"

(ix) FEATURE:
(A) NAME/KEY: misc_feature
(B) LOCATION: group(13, 17)
(D) OTHER INFORMATION: /note= "A represents a nucleotide comprising an adenine, preferably an adenine deoxyribonucleotide"

(ix) FEATURE:
(A) NAME/KEY: misc_feature
(B) LOCATION: 3
(D) OTHER INFORMATION: /note= "May also be any nucleotide comprising a pyrimidine, preferably a cytosine, a 5-methyl cytosine, or a thymidine deoxyribonucleotide"

(ix) FEATURE:
(A) NAME/KEY: misc_feature
(B) LOCATION: 10
(D) OTHER INFORMATION: /note= "Preferably a nucleotide comprising guanine, more preferably a guanine deoxyribonucleotide"

(xi) SEQUENCE DESCRIPTION: SEQ ID NO:4:

NTYNYNRYNN NNAYRRAN                                                                                      18

(2) INFORMATION FOR SEQ ID NO:5:

(i) SEQUENCE CHARACTERISTICS:
(A) LENGTH: 42 base pairs
(B) TYPE: nucleic acid
(C) STRANDEDNESS: single
(D) TOPOLOGY: circular (xi) SEQUENCE DESCRIPTION: SEQ ID NO:5:

TTTCCCCTAG CAACAGATGT TTTTCATCTG TTGCTAGGGG TT                                                            42

(2) INFORMATION FOR SEQ ID NO:6:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:6:

CTAGGGGTTT TCCCCTAGCA ACAGATGTTT TCATCTGTTG                                                              40

(2) INFORMATION FOR SEQ ID NO:7:

(i) SEQUENCE CHARACTERISTICS:
(A) LENGTH: 40 base pairs
(B) TYPE: nucleic acid
(C) STRANDEDNESS: single
(D) TOPOLOGY: linear ( x i ) SEQUENCE DESCRIPTION: SEQ ID NO:7:

GACTGGGTTT TCCCAGTCCA TACGAAGTTT TCTTCGTATG                                                40

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GCTAGGGGTT TTTCCCCTAG CAACAGATGT TTTTCATCTG TT                                             42

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CTAGGGGTTT TTCCCCTAGC AACAGATGTT TTTCATCTGT TG                                             42

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TAACAACTTT TGTTGTTATA GTAACTTTTG TTACTA                                                    36

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TCCCTTGGTT TTCCAAGGGA CTTTCCGCTT TTGCGGAAAG                                                40

( 2 ) INFORMATION FOR SEQ ID NO:12:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TGCTAGGTTT TTCCTAGCAA CAGATGTTTT TCATCTGT                                                  38

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

```
    Pro   Lys   Lys   Lys   Arg   Lys   Val
     1                 5
```

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GCTAGGGGTT TTTCCCCTAG CAACAGATGT TTTTCATCTG TT        42

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TATACGGGTT TTCCCGTATA CCACTCTGTT TTCAGAGTGG        40

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TGAGTTGGTT TTCCAACTCA CTTTCCGCTT TTGCGGAAAG        40

( 2 ) INFORMATION FOR SEQ ID NO:17:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TCCCTTGGTT TTCCAAGGGA CTTTCCGCTT TTGCGGAAAG        40

( 2 ) INFORMATION FOR SEQ ID NO:18:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TAACAACTTT TGTTGTTATA GTAACTTTG TTACTA        36

( 2 ) INFORMATION FOR SEQ ID NO:19:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CTAGGGGTTT TTCCCCTAGC AACAGATGTT TTTCATCTGT TG        42

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GCCACGGAGC GAGACATCTC    20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:21:

GCCACGGAGC GAGACATCTC    20

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:22:

GAGATGTCTC GCTCCGTGGC    20

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:23:

TTTTCCCCTA GCAACAGATG TTTTCATCTG TTGCTAGGGG    40